United States Patent [19]

Watanabe et al.

[11] Patent Number: 5,229,395

[45] Date of Patent: Jul. 20, 1993

[54] POTENTIAL ANTICANCER AGENTS DERIVED FROM ACRIDINE

[75] Inventors: Kyoichi A. Watanabe, Rye Brook, N.Y.; Kiyobumi Takahashi, Tokyo, Japan

[73] Assignee: Sloan-Kettering Institute For Cancer Research, New York, N.Y.

[21] Appl. No.: 754,283

[22] Filed: Aug. 30, 1991

Related U.S. Application Data

[63] Continuation of Ser. No. 422,629, Oct. 17, 1989, abandoned.

[51] Int. Cl.$^5$ ............... C07D 219/10; A61K 31/435
[52] U.S. Cl. ............................ 514/297; 546/105
[58] Field of Search ..................... 546/105; 514/297

[56] References Cited

FOREIGN PATENT DOCUMENTS

91/05770  5/1991  World Int. Prop. O. .

OTHER PUBLICATIONS

Ferguson et al., Journ. of medicinal chemistry vol. 22 No. 3 pp. 251-255 (1978).

Primary Examiner—Nicholas S. Rizzo
Attorney, Agent, or Firm—John P. White

[57] ABSTRACT

The compounds of the subject invention can be represented as follows:

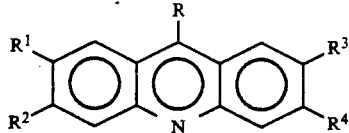

wherein each of $R^1$, $R^2$, $R^3$, $R^4$, are the same or different and are hydrogen (H), or a lower alkyl group of from about 1-4 carbon atoms, or a lower alkoxy group of from about 1-4 carbon atoms.

R is a substituted aniline.

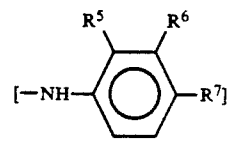

wherein one of $R^5$, $R^6$, $R^7$ is an alkanol having the formula $-(CH_2)_nOH$, $n=1-4$, or its carbamate ester having the formula $-(CH_2)_nOCONR'R''$, $n=1-4$, and wherein $R'$ and $R''$ the same or different lower alkyl groups of from about 1 to 4 carbon atoms, one of $R'$ and $R''$ may be hydrogen (H), and the remaining groups are hydrogen.

Additionally, the subject invention provides methods for synthesizing the above-identified compounds, physiologically acceptable compositions containing these compounds and methods for using these compounds to inhibit the growth of tumor cells.

5 Claims, 2 Drawing Sheets

1A  X=H
1B  X=OH

2A  R=H
2B  R=OMe

3A  R=H
3B  R=OMe

POTENTIAL ANTICANCER AGENTS DERIVED FROM ACRIDINE

The invention described herein was made in the course of work under Grant Nos. CA-08748 and CA-18856 from the National Cancer Institute, National Institutes of Health, U.S. Department of Health and Human Services. The U.S. Government may have certain rights in this application.

This is a continuation of application Ser. No. 422,629, filed Oct. 17, 1989 now abandoned.

BACKGROUND OF THE INVENTION

Recently, a novel type of potential anticancer agent has been developed [Koyama, Kelly and Watanabe, U.S. Ser. No. 302,836, filed Jan. 27, 1989] now U.S. Pat. No. 4,966,918 which contains both intercalating and alkylating capabilities. Chrysophanol (1A, FIG. 1) and emodin (1B) were converted into 3-[N,N-bis(2-chloroethyl)-amino]methyl-1,8-dihydroxy-9,10-anthraquinone (3A) and its 6-methoxy analog (3B) via the respective 1,8-dimethoxy intermediates (2A and 2B). The natural products, 1A and 1B, may have the intercalating capability but lack the alkylating function, whereas 2A and 2B may have the alkylating capability but are incapable of intercalating into DNA due to the presence of two bulky methoxy groups. These compounds are practically inactive against mouse leukemic cells L1210 in tissue culture. However, 3A and 3B which contain both intercalating and alkylating capabilities exhibited potent inhibitory activity against L1210 cells in tissue culture.

A recent publication [Koyama, Kelly and Watanabe, J. Med. Chem., 31:283-284 (1988)], showed that planar molecules with basic nature can interact with DNA more strongly than the neutral species. On the basis of the above considerations and discoveries, the present invention was developed.

SUMMARY OF THE INVENTION

Compounds of the invention can be represented by formula I as follows:

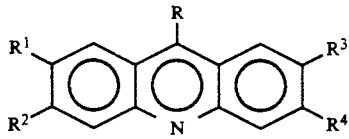

wherein each of $R^1$, $R^2$, $R^3$, $R^4$, are the same or different and are hydrogen (H), or a lower alkyl group of from about 1-4 carbon atoms, or a lower alkoxy group of from about 1-4 carbon atoms.

R is a substituted aniline

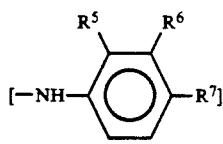

wherein one of $R^5$, $R^6$, $R^7$ is an alkanol having the formula —$(CH_2)_n$OH, n=1-4, or its carbamate ester having the formula —$(CH_2)_n$OCONR'R", n=1-4, and wherein R' and R" the same or different lower alkyl groups of from about 1 to 4 carbon atoms such as methyl, ethyl, n-propyl or i-propyl, one of R' and R" may be hydrogen (H), and the remaining groups are hydrogen.

DETAILED DESCRIPTION OF THE INVENTION

Figure 1:
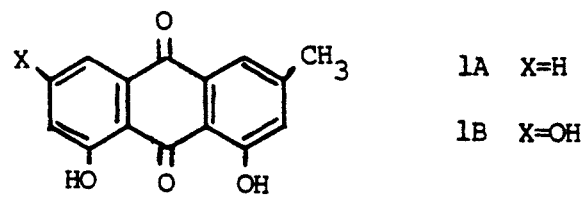
FIG. 1: Structures of compounds with properties related to the compound of the subject invention. 1A is chrysophanol; 1B is emodin; 2A is a 1,8 dimethoxy derivative of 1B; 3A is 3-[N,N-bis (2-chloroethyl)-amino]methyl-1,8-dihydroxy-9,10-anthraquinone; and 3B is the 6-methoxy analog of 3A.
Figure 1:
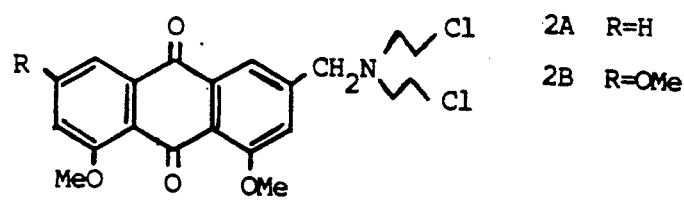
Figure 1:
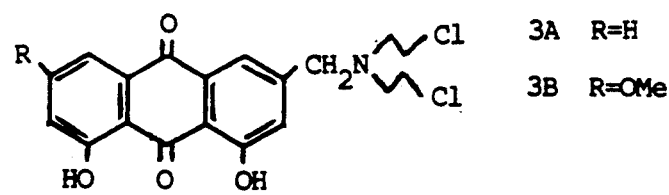

The subject invention provides a compound having the structure:

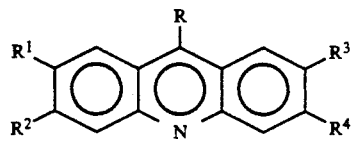

wherein each of $R^1$, $R^2$, $R^3$, $R^4$, are the same or different and are hydrogen (H), or a lower alkyl group of from 1-4 carbon atoms, or a lower alkoxy group of from about 1-4 carbon atoms. R is a substituted aniline

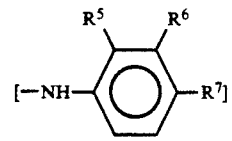

wherein one of $R^5$, $R^6$, $R^7$ is an alkanol having the formula —$(CH_2)_n$OH, n=1-4, or its carbamate ester having the formula —$(CH_2)_n$OCONR'R", n=1-4, and wherein R' and R" are the same or different lower alkyl groups of from about 1 to 4 carbon atoms, one of R' and R" may be hydrogen (H), and the remaining groups are hydrogen.

Compounds having the above-identified structure, although not limited to the following compounds, may be selected from the group consisting of:

9-(2'-Hydroxymethyl)anilinoacridine,
9-(2'-Hydroxymethyl)anilino-2-methoxyacridine,
9-(3'-Hydroxymethyl)anilinoacridine,
9-(3'-Hydroxymethyl)anilino-2-methoxyacridine,
9-(3'-Hydroxymethyl)anilino-3-methoxyacridine,
9-(3'-Hydroxymethyl)anilino-2-methylacridine,
9-(3'-Hydroxymethyl)anilino-3-methylacridine,
9-(3'-Hydroxymethyl)anilino-2-methoxy-6-methylacridine,
9-(3'-Hydroxymethyl)anilino-2-methoxy-7-methylacridine,
9-(3'-Hydroxymethyl)anilino-2,6-dimethoxyacridine,
9-(3'-Hydroxymethyl)anilino-2,7-dimethoxyacridine,
9-(3'-Hydroxymethyl)anilino-3-methoxy-6-methylacridine,
9-(3'-Hydroxymethyl)anilino-6-methoxy-2-methylacridine,
9-(3'-Hydroxymethyl)anilino-3,6-dimethoxyacridine
9-(3'-Hydroxymethyl)anilino-2,6-dimethylacridine,
9-(3'-Hydroxymethyl)anilino-2,7-dimethylacridine,
9-(3'-Hydroxymethyl)anilino-3,6-dimethylacridine, 9-(3'-Hydroxymethyl)anilino-7-methoxy-2,3-dimethylacridine,
9-(3'-Hydroxymethyl)anilino-2,6-dimethoxy-7-methylacridine,
9-(3'-Hydroxymethyl)anilino-2,7-dimethoxy-3-methylacridine,
9-(3'-Hydroxymethyl)anilino-2,3,7-trimethoxyacridine,
9-(3'-Hydroxymethyl)anilino-6-methoxy-2,3-dimethylacridine,
9-(3'-Hydroxymethyl)anilino-3,6-dimethoxy-2-methylacridine,
9-(3'-Hydroxymethyl)anilino-2,6-dimethoxy-3-methylacridine,
9-(3'-Hydroxymethyl)anilino-2,3,6-trimethoxyacridine,
9-(3'-Hydroxymethyl)anilino-3-methoxy-2,7-dimethylacridine,
9-(3'-Hydroxymethyl)anilino-2-methoxy-3,7-dimethylacridine,
9-(3'-Hydroxymethyl)anilino-2,3-dimethoxy-7-methylacridine,
9-(3'-Hydroxymethyl)anilino-2,3,7-trimethylacridine,
9-(3'-Hydroxymethyl)anilino-3-methoxy-2,6-dimethylacridine,
9-(3'-Hydroxymethyl)anilino-2-methoxy-3,6-dimethylacridine,
9-(3'-Hydroxymethyl)anilino-2,3-dimethoxy-6-methylacridine,
9-(3'-Hydroxymethyl)anilino-2,3,6-trimethylacridine,
9-(3'-Hydroxymethyl)anilino-2,3-dimethoxy-6,7-dimethylacridine,
9-(3'-Hydroxymethyl)anilino-2,3,6-trimethoxy-7-methylacridine,
9-(3'-Hydroxymethyl)anilino-2,3,7-trimethoxy-6-methylacridine,
9-(3'-Hydroxymethyl)anilino-2,3,6,7-tetramethoxyacridine,
9-(3'-Hydroxymethyl)anilino-2-methoxy-3,6,7-trimethylacridine,
9-(3'-Hydroxymethyl)anilino-3-methoxy-2,6,7-trimethylacridine,
9-(3'-Hydroxymethyl)anilino-2,3,6,7-tetramethylacridine,
9-(4'-Hydroxymethyl)anilinoacridine,
9-(4'-Hydroxymethyl)anilino-2-methoxyacridine,
9-(4'-Hydroxymethyl)anilino-3-methoxyacridine,
9-(4'-Hydroxymethyl)anilino-2-methylacridine,
9-(4'-Hydroxymethyl)anilino-3-methylacridine,
9-(4'-Hydroxymethyl)anilino-2-methoxy-6-methylacridine,
9-(4'-Hydroxymethyl)anilino-2-methoxy-7-methylacridine,
9-(4'-Hydroxymethyl)anilino-2,6-dimethoxyacridine,
9-(4'-Hydroxymethyl)anilino-2,7-dimethoxyacridine,
9-(4'-Hydroxymethyl)anilino-3-methoxy-6-methylacridine,
9-(4'-Hydroxymethyl)anilino-6-methoxy-2-methylacridine,
9-(4'-Hydroxymethyl)anilino-3,6-dimethoxyacridine,
9-(4'-Hydroxymethyl)anilino-2,6-dimethylacridine,
9-(4'-Hydroxymethyl)anilino-2,7-dimethylacridine,
9-(4'-Hydroxymethyl)anilino-3,6-dimethylacridine,
9-(4'-Hydroxymethyl)anilino-7-methoxy-2,3-dimethylacridine,
9-(4'-Hydroxymethyl)anilino-2,6-dimethoxy-7-methylacridine,
9-(4'-Hydroxymethyl)anilino-2,7-dimethoxy-6-methylacridine,
9-(4'-Hydroxymethyl)anilino-2,3,7-trimethoxyacridine,
9-(4'-Hydroxymethyl)anilino-6-methoxy-2,3-dimethylacridine,
9-(4'-Hydroxymethyl)anilino-3,6-dimethoxy-2-methylacridine,
9-(4'-Hydroxymethyl)anilino-2,6-dimethoxy-3-methylacridine,
9-(4'-Hydroxymethyl)anilino-2,3,6-trimethoxyacridine,
9-(4'-Hydroxymethyl)anilino-3-methoxy-2,7-dimethylacridine,
9-(4'-Hydroxymethyl)anilino-2-methoxy-3,7-dimethylacridine,
9-(4'-Hydroxymethyl)anilino-2,3-dimethoxy-7-methylacridine,
9-(4'-Hydroxymethyl)anilino-2,3,7-trimethylacridine,
9-(4'-Hydroxymethyl)anilino-3-methoxy-2,6-dimethylacridine,
9-(4'-Hydroxymethyl)anilino-2-methoxy-3,6-dimethylacridine,
9-(4'-Hydroxymethyl)anilino-2,3-dimethoxy-6-methylacridine,
9-(4'-Hydroxymethyl)anilino-2,3,6-trimethylacridine,
9-(4'-Hydroxymethyl)anilino-2,3-dimethoxy-6,7-dimethylacridine,
9-(4'-Hydroxymethyl)anilino-2,3,6-trimethoxy-7-methylacridine,
9-(4'-Hydroxymethyl)anilino-2,3,7-trimethoxy-6-methylacridine,
9-(4'-Hydroxymethyl)anilino-2,3,6,7-tetramethoxyacridine,
9-(4'-Hydroxymethyl)anilino-2-methoxy-3,6,7-trimethylacridine,
9-(4'-Hydroxymethyl)anilino-2,6,7-trimethylacridine,
9-(4'-Hydroxymethyl)anilino-2,3,6,7-tetramethylacridine,
9-[2'-(β-Hydroxyethyl)anilinoacridine,
9-[2'-(β-Hydroxyethyl)anilino-2-methoxyacridine,
9-[3'-(β-Hydroxyethyl)anilinoacridine,
9-[3'-(β-Hydroxyethyl)anilino-2-methoxyacridine,
9-[3'-(β-Hydroxyethyl)anilino-3-methoxyacridine,
9-[3'-(β-Hydroxyethyl)anilino-2-methylacridine,
9-[3'-(β-Hydroxyethyl)anilino-3-methylacridine,
9-[3'-(β-Hydroxyethyl)anilino-2-methoxy-6-methylacridine,
9-[3'-(β-Hydroxyethyl)anilino-2-methoxy-7-methylacridine,
9-[3'-(β-Hydroxyethyl)anilino-2,6-dimethoxyacridine,
9-[3'-(β-Hydroxyethyl)anilino-2,7-dimethoxyacridine,
9-[3'-(β-Hydroxyethyl)anilino-3-methoxy-6-methylacridine,
9-[3'-(β-Hydroxyethyl)anilino-6-methoxy-2-methylacridine,
9-[3'-(β-Hydroxyethyl)anilino-3,6-dimethoxyacridine,
9-[3'-(β-Hydroxyethyl)anilino-2,6-dimethylacridine,
9-[3'-(β-Hydroxyethyl)anilino-2,7-dimethylacridine,
9-[3'-(β-Hydroxyethyl)anilino-3,6-dimethylacridine,
9-[3'-(β-Hydroxyethyl)anilino-7-methoxy-2,3-dimethylacridine,
9-[3'-(β-Hydroxyethyl)anilino-3,7-dimethoxy-2-methylacridine,
9-[3'-(β-Hydroxyethyl)anilino-2,7-dimethoxy-3-methylacridine,
9-[3'-(β-Hydroxyethyl)anilino-2,3,7-trimethoxyacridine,
9-[3'-(β-Hydroxyethyl)anilino-6-methoxy-2,3-dimethylacridine,
9-[3'-(β-Hydroxyethyl)anilino-3,6-dimethoxy-2-methylacridine, 9-[3'-(β-Hydroxyethyl)anilino-2,6-dimethoxy-3-methylacridine,
9-[3'-(β-Hydroxyethyl)anilino-2,3,6-trimethoxyacridine,
9-[3'-(β-Hydroxyethyl)anilino-3-methoxy-2,7-dimethylacridine,
9-[3'-(β-Hydroxyethyl)anilino-2-methoxy-3,7-dimethylacridine,
9-[3'-(β-Hydroxyethyl)anilino-2,3-dimethoxy-7-methylacridine,
9-[3'-(β-Hydroxyethyl)anilino-2,3,7-trimethylacridine,
9-[3'-(β-Hydroxyethyl)anilino-3-methoxy-2,6-dimethylacridine,
9-[3'-(β-Hydroxyethyl)anilino-2-methoxy-3,6-dimethylacridine,
9-[3'-(β-Hydroxyethyl)anilino-2,3-dimethoxy-6-methylacridine,
9-[3'-(β-Hydroxyethyl)anilino-2,3,6-trimethylacridine,
9-[3'-(β-Hydroxyethyl)anilino-2,3-dimethoxy-6,7-dimethylacridine,
9-[3'-(β-Hydroxyethyl)anilino-2,3,6-trimethoxy-7-methylacridine,
9-[3'-(β-Hydroxyethyl)anilino-2,3,7-trimethoxy-6-methylacridine,
9-[3'-(β-Hydroxyethyl)anilino-2,3,6,7tetramethoxyacridine,
9-[3'-(β-Hydroxyethyl)anilino-2-methoxy-3,6,7-trimethylacridine,
9-[3'-(β-Hydroxyethyl)anilino-3-methoxy-2,6,7-trimethylacridine,
9-[3'-(β-Hydroxyethyl)anilino-2,3,6,7-tetramethylacridine,
9-[4'-(β-Hydroxyethyl)anilinoacridine,
9-[4'-(β-Hydroxyethyl)anilino-2-methoxyacridine,
9-[4'-(β-Hydroxyethyl)anilino-3-methoxyacridine,
9-[4'-(β-Hydroxyethyl)anilino-2-methylacridine,
9-[4'-(β-Hydroxyethyl)anilino-3-methylacridine,
9-[4'-(β-Hydroxyethyl)anilino-2-methoxy-6-methylacridine,
9-[4'-(β-Hydroxyethyl)anilino-2-methoxy-7-methylacridine,
9-[4'-(β-Hydroxyethyl)anilino-2,6-dimethoxyacridine,
9-[4'-(β-Hydroxyethyl)anilino-2,7-dimethoxyacridine,
9-[4'-(β-Hydroxyethyl)anilino-3-methoxy-6-methylacridine,
9-[4'-(β-Hydroxyethyl)anilino-6-methoxy-2-methylacridine,
9-[4'-(β-Hydroxyethyl)anilino-3,6-dimethoxyacridine,
9-[4'-(β-Hydroxyethyl)anilino-2,6-dimethylacridine,
9-[4'-(β-Hydroxyethyl)anilino-2,7-dimethylacridine,
9-[4'-(β-Hydroxyethyl)anilino-3,6-dimethylacridine,
9-[4'-(β-Hydroxyethyl)anilino-7-methoxy-2,3-dimethylacridine,
9-[4'-(β-Hydroxyethyl)anilino-3,7-dimethoxy-2-methylacridine,
9-[4'-(β-Hydroxyethyl)anilino-2,7-dimethoxy-2-methylacridine,
9-[4'-(β-Hydroxyethyl)anilino-2,3,7-trimethoxyacridine,
9-[4'-(β-Hydroxyethyl)anilino-6-methoxy-2,3-dimethylacridine,
9-[4'-(β-Hydroxyethyl)anilino-3,6-dimethoxy-2-methylacridine,
9-[4'-(β-Hydroxyethyl)anilino-2,6-dimethoxy-3-methylacridine,
9-[4'-(β-Hydroxyethyl)anilino-2,3,6-trimethoxyacridine,
9-[4'-(β-Hydroxyethyl)anilino-3-methoxy-2,7-dimethylacridine,
9-[4'-(β-Hydroxyethyl)anilino-2-methoxy-3,7-dimethylacridine,
9-[4'-(β-Hydroxyethyl)anilino-2,3-dimethoxy-7-methylacridine,
9-[4'-(β-Hydroxyethyl)anilino-2,3,7-trimethylacridine,
9-[4'-(β-Hydroxyethyl)anilino-3-methoxy-2,6-dimethylacridine,
9-[4'-(β-Hydroxyethyl)anilino-2-methoxy-3,6-dimethylacridine,
9-[4'-(β-Hydroxyethyl)anilino-2,3-dimethoxy-6-methylacridine,
9-[4'-(β-Hydroxyethyl)anilino-2,3,6-trimethylacridine,
9-[4'-(β-Hydroxyethyl)anilino-2,3-dimethoxy-6,7-dimethylacridine,
9-[4'-(β-Hydroxyethyl)anilino-2,3,6-trimethoxy-7-methylacridine,
9-[4'-(β-Hydroxyethyl)anilino-2,3,7-trimethoxy-6-methylacridine,
9-[4'-(β-Hydroxyethyl)anilino-2,3,6,7-tetramethoxyacridine,
9-[4'-(β-Hydroxyethyl)anilino-2-methoxy-3,6,7-trimethylacridine,
9-[4'-(β-Hydroxyethyl)anilino-3-methoxy-2,6,7-trimethylacridine,
9-[4'-(β-Hydroxyethyl)anilino-2,3,6,7-tetramethoxyacridine.

Compounds having the above-identified structure may also be selected from the group consisting of, but not limited to:
9-[2'-(Methylaminocarbonyloxymethyl)anilino]acridine,
9-[2'-(Isopropylaminocarbonyloxymethyl)anilino]-acridine,
9-[3'-(Methylaminocarbonyloxymethyl)anilino]acridine,
9-[3'-(Methylaminocarbonyloxymethyl)anilino]-2-methoxyacridine,
9-[3'-(Methylaminocarbonyloxymethyl)anilino]-3-methoxyacridine,
9-[3'-(Methylaminocarbonyloxymethyl)anilino]-2-methylacridine,
9-[3'-(Methylaminocarbonyloxymethyl)anilino]-3-methylacridine,
9-[3'-(Methylaminocarbonyloxymethyl)anilino]-2-methoxy-6-methylacridine,
9-[3'-(Methylaminocarbonyloxymethyl)anilino]-2-methoxy-7-methylacridine,
9-[3'-(Methylaminocarbonyloxymethyl)anilino]-2,6-dimethoxyacridine,
9-[3'-(Methylaminocarbonyloxymethyl)anilino]-2,7-dimethoxyacridine,
9-[3'-(Methylaminocarbonyloxymethyl)anilino]-3-methoxy-6-methylacridine,
9-[3'-(Methylaminocarbonyloxymethyl)anilino]-6-methoxy-2-methylacridine,
9-[3'-(Methylaminocarbonyloxymethyl)anilino]-3,6-dimethoxyacridine,
9-[3'-(Methylaminocarbonyloxymethyl)anilino]-2,6-dimethylacridine,
9-[3'-(Methylaminocarbonyloxymethyl)anilino]-3,6-dimethylacridine,
9-[3'-(Methylaminocarbonyloxymethyl)anilino]-7-methoxy-2,3-dimethylacridine,
9-[3'-(Methylaminocarbonyloxymethyl)anilino]-2,6-dimethoxy-7-methylacridine, 9-[3'-(Methylaminocarbonyloxymethyl)anilino]-2,7-dimethoxy-3-methylacridine,
9-[3'-(Methylaminocarbonyloxymethyl)anilino]-2,3,7-trimethoxyacridine,
9-[3'-(Methylaminocarbonyloxymethyl)anilino]-6-methoxy-2,3-dimethylacridine,
9-[3'-(Methylaminocarbonyloxymethyl)anilino]-3,6-dimethoxy-2-methylacridine,
9-[3'-(Methylaminocarbonyloxymethyl)anilino]-2,3,6-trimethoxyacridine,
9-[3'-(Methylaminocarbonyloxymethyl)anilino]-3-methoxy-2,7-dimethylacridine,
9-[3'-(Methylaminocarbonyloxymethyl)anilino]-2-methoxy-3,7-dimethylacridine,
9-[3'-(Methylaminocarbonyloxymethyl)anilino]-2,3-dimethoxy-7-methylacridine,
9-[3'-(Methylaminocarbonyloxymethyl)anilino]-2,3,7-trimethylacridine,
9-[3'-(Methylaminocarbonyloxymethyl)anilino]-3-methoxy-2,6-dimethylacridine,
9-[3'-(Methylaminocarbonyloxymethyl)anilino]-2-methoxy-3,6-dimethylacridine,
9-[3'-(Methylaminocarbonyloxymethyl)anilino]-2,3-dimethoxy-6-methylacridine,
9-[3'-(Methylaminocarbonyloxymethyl)anilino]-2,3,6-trimethylacridine,
9-[3'-(Methylaminocarbonyloxymethyl)anilino]-2,3-dimethoxy-6,7-dimethylacridine,
9-[3'-(Methylaminocarbonyloxymethyl)anilino]-2,3,6-trimethoxy-7-methylacridine,
9-[3'-(Methylaminocarbonyloxymethyl)anilino]-2,3,7-trimethoxy-6-methylacridine,
9-[3'-(Methylaminocarbonyloxymethyl)anilino]-2,3,6,7-tetramethoxyacridine,
9-[3'-(Methylaminocarbonyloxymethyl)anilino]-2-methoxy-3,6,7-trimethylacridine,
9-[3'-(Methylaminocarbonyloxymethyl)anilino]-3-methoxy-2,6,7-trimethylacridine,
9-[3'-(Methylaminocarbonyloxymethyl)anilino]-2,3,6,7-tetramethylacridine,
9-[3'-(Isopropylaminocarbonyloxymethyl)anilino]acridine,
9-[3'-(Isopropylaminocarbonyloxymethyl)anilino]-2-methoxyacridine,
9-[3'-(Isopropylaminocarbonyloxymethyl)anilino]-3-methoxyacridine,
9-[3'-(Isopropylaminocarbonyloxymethyl)anilino]-2-methylacridine,
9-[3'-(Isopropylaminocarbonyloxymethyl)anilino]-3-methylacridine,
9-[3'-(Isopropylaminocarbonyloxymethyl)anilino]-2-methoxy-6-methylacridine,
9-[3'-(Isopropylaminocarbonyloxymethyl)anilino]-2-methoxy-7-methylacridine,
9-[3'-(Isopropylaminocarbonyloxymethyl)anilino]-2,6-dimethoxyacridine,
9-[3'-(Isopropylaminocarbonyloxymethyl)anilino]-3-methoxy-6-methylacridine,
9-[3'-(Isopropylaminocarbonyloxymethyl)anilino]-6-methoxy-2-methylacridine,
9-[3'-(Isopropylaminocarbonyloxymethyl)anilino]-3,6-dimethoxyacridine,
9-[3'-(Isopropylaminocarbonyloxymethyl)anilino]-2,6-dimethylacridine,
9-[3'-(Isopropylaminocarbonyloxymethyl)anilino]-2,7-dimethylacridine,
9-[3'-(Isopropylaminocarbonyloxymethyl)anilino]-3,6-dimethylacridine,
9-[1'-(Isopropylaminocarbonyloxymethyl)anilino]-7-methoxy-2,3-dimethylacridine,
9-[3'-(Isopropylaminocarbonyloxymethyl)anilino]-2,6-dimethoxy-7-dimethylacridine,
9-[3'-(Isopropylaminocarbonyloxymethyl)anilino]-2,7-dimethoxy-3-dimethylacridine,
9-[3'-(Isopropylaminocarbonyloxymethyl)anilino]-2,3,7-trimethoxyacridine,
9-[3'-(Isopropylaminocarbonyloxymethyl)anilino]-6-methoxy-2,3-dimethylacridine,
9-[3'-(Isopropylaminocarbonyloxymethyl)anilino]-3,6-dimethoxy-2-methylacridine,
9-[3'-(Isopropylaminocarbonyloxymethyl)anilino]-2,6-dimethoxy-3-methylacridine,
9-[3'-(Isopropylaminocarbonyloxymethyl)anilino]-2,3,6-trimethoxyacridine,
9-[3'-(Isopropylaminocarbonyloxymethyl)anilino]-3-methoxy-2,7-dimethylacridine,
9-[3'-(Isopropylaminocarbonyloxymethyl)anilino]-2-methoxy-3,7-dimethylacridine,
9-[3'-(Isopropylaminocarbonyloxymethyl)anilino]-2,3-methoxy-7-methylacridine,
9-[3'-(Isopropylaminocarbonyloxymethyl)anilino]-2,3,7-trimethylacridine,
9-[3'-(Isopropylaminocarbonyloxymethyl)anilino]-3-methoxy-2,6-dimethylacridine,
9-[3'-(Isopropylaminocarbonyloxymethyl)anilino]-2-methoxy-3,6-dimethylacridine,
9-[3'-(Isopropylaminocarbonyloxymethyl)anilino]-2,3-dimethoxy-6-methylacridine,
9-[3'-(Isopropylaminocarbonyloxymethyl)anilino]-2,3,6-trimethylacridine,
9-[3'-(Isopropylaminocarbonyloxymethyl)anilino]-2,3-dimethoxy-6,7-dimethylacridine,
9-[3'-(Isopropylaminocarbonyloxymethyl)anilino]-2,3,6-trimethoxy-7-methylacridine,
9-[3'-(Isopropylaminocarbonyloxymethyl)anilino]-2,3,7-trimethoxy-6-methylacridine,
9-[3'-(Isopropylaminocarbonyloxymethyl)anilino]-2,3,6,7-tetramethoxyacridine,
9-[3'-(Isopropylaminocarbonyloxymethyl)anilino]-2-methoxy-3,6,7-trimethylacridine,
9-[3'-(Isopropylaminocarbonyloxymethyl)anilino]-3-methoxy-2,6,7-trimethylacridine,
9-[3'-(Isopropylaminocarbonyloxymethyl)anilino]-2,3,6,7-tetramethylacridine,
9-[4'-(Methylaminocarbonyloxymethyl)anilino]acridine,
9-[4'-(Methylaminocarbonyloxymethyl)anilino]-2-methoxyacridine,
9-[4'-(Methylaminocarbonyloxymethyl)anilino]-3-methoxyacridine,
9-[4'-(Methylaminocarbonyloxymethyl)anilino]-2-methylacridine,
9-[4'-(Methylaminocarbonyloxymethyl)anilino]-3-methylacridine,
9-[4'-(Methylaminocarbonyloxymethyl)anilino]-2-methoxy-6-methylacridine,
9-[4'-(Methylaminocarbonyloxymethyl)anilino]-2-methoxy-7-methylacridine,
9-[4'-(Methylaminocarbonyloxymethyl)anilino]-2,6-dimethoxyacridine,
9-[4'-(Methylaminocarbonyloxymethyl)anilino]-2,7-dimethoxyacridine,
9-[4'-(Methylaminocarbonyloxymethyl)anilino]-3-methoxy-6-methylacridine,
9-[4'-(Methylaminocarbonyloxymethyl)anilino]-6-methoxy-2-methylacridine, 9-[4'-(Methylaminocarbonyloxymethyl)anilino]-3,6-dimethoxyacridine,
9-[4'-(Methylaminocarbonyloxymethyl)anilino]-2,6-dimethylacridine,
9-[4'-(Methylaminocarbonyloxymethyl)anilino]-2,7-dimethylacridine,
9-[4'-(Methylaminocarbonyloxymethyl)anilino]-3,6-dimethylacridine,
9-[4'-(Methylaminocarbonyloxymethyl)anilino]-2,6-dimethoxy-7-methylacridine,
9-[4'-(Methylaminocarbonyloxymethyl)anilino]-2,7-dimethoxy-7-methylacridine,
9-[4'-(Methylaminocarbonyloxymethyl)anilino]-2,3,7-trimethoxyacridine,
9-[4'-(Methylaminocarbonyloxymethyl)anilino]-6-methoxy-2,3-dimethylacridine,
9-[4'-(Methylaminocarbonyloxymethyl)anilino]-3,6-dimethoxy-2-methylacridine,
9-[4'-(Methylaminocarbonyloxymethyl)anilino]-2,6-dimethoxy-3-methylacridine,
9-[4'-(Methylaminocarbonyloxymethyl)anilino]-2,3,6-trimethoxyacridine,
9-[4'-(Methylaminocarbonyloxymethyl)anilino]-3-methoxy-2,7-dimethylacridine,
9-[4'-(Methylaminocarbonyloxymethyl)anilino]-2-methoxy-3,7-dimethylacridine,
9-[4'-(Methylaminocarbonyloxymethyl)anilino]-2,3-dimethoxy-7-methylacridine,
9-[4'-(Methylaminocarbonyloxymethyl)anilino]-2,3,7-trimethylacridine,
9-[4'-(Methylaminocarbonyloxymethyl)anilino]-3-methoxy-2,6-dimethylacridine,
9-[4'-(Methylaminocarbonyloxymethyl)anilino]-2-methoxy-3,6-dimethylacridine,
9-[4'-(Methylaminocarbonyloxymethyl)anilino]-2,3-dimethoxy-6-methylacridine,
9-[4'-(Methylaminocarbonyloxymethyl)anilino]-2,3,6-trimethylacridine,
9-[4'-(Methylaminocarbonyloxymethyl)anilino]-2,3-dimethoxy-6,7-dimethylacridine,
9-[4'-(Methylaminocarbonyloxymethyl)anilino]-2,3,6-trimethoxy-7-methylacridine,
9-[4'-(Methylaminocarbonyloxymethyl)anilino]-2,3,7-trimethoxy-6-methylacridine,
9-[4'-(Methylaminocarbonyloxymethyl)anilino]-2,3,6,7-tetramethoxyacridine,
9-[4'-(Methylaminocarbonyloxymethyl)anilino]-2-methoxy-3,6,7-trimethylacridine,
9-[4'-(Methylaminocarbonyloxymethyl)anilino]-3-methoxy-2,6,7-trimethylacridine,
9-[4'-(Methylaminocarbonyloxymethyl)anilino]-2,3,6,7-tetramethylacridine,
9-[4'-(Isopropylaminocarbonyloxymethyl)anilino]acridine,
9-[4'-(Isopropylaminocarbonyloxymethyl)anilino]-2-methoxyacridine,
9-[4'-(Isopropylaminocarbonyloxymethyl)anilino]-3-methoxyacridine,
9-[4'-(Isopropylaminocarbonyloxymethyl)anilino]-2-methylacridine,
9-[4'-(Isopropylaminocarbonyloxymethyl)anilino]-3-methylacridine,
9-[4'-(Isopropylaminocarbonyloxymethyl)anilino]-2-methoxy-6-methylacridine,
9-[4'-(Isopropylaminocarbonyloxymethyl)anilino]-2-methoxy-7-methylacridine,
9-[4'-(Isopropylaminocarbonyloxymethyl)anilino]-2,6-dimethoxyacridine,
9-[4'-(Isopropylaminocarbonyloxymethyl)anilino]-2,7-dimethoxyacridine,
9-[4'-(Isopropylaminocarbonyloxymethyl)anilino]-3-methoxy-6-methylacridine,
9-[4'-(Isopropylaminocarbonyloxymethyl)anilino]-6-methoxy-2-methylacridine,
9-[4'-(Isopropylaminocarbonyloxymethyl)anilino]-3,6-dimethoxyacridine,
9-[4'-(Isopropylaminocarbonyloxymethyl)anilino]-2,6-dimethylacridine,
9-[4'-(Isopropylaminocarbonyloxymethyl)anilino]-2,7-dimethylacridine,
9-[4'-(Isopropylaminocarbonyloxymethyl)anilino]-3,6-dimethylacridine,
9-[4'-(Isopropylaminocarbonyloxymethyl)anilino]-7-methoxy-2,3-dimethylacridine,
9-[4'-(Isopropylaminocarbonyloxymethyl)anilino]-2,6-dimethoxy-7-dimethylacridine,
9-[4'-(Isopropylaminocarbonyloxymethyl)anilino]-2,7-dimethoxy-3-methylacridine,
9-[4'-(Isopropylaminocarbonyloxymethyl)anilino]-2,3,7-trimethoxyacridine,
9-[4'-(Isopropylaminocarbonyloxymethyl)anilino]-6-methoxy-2,3-dimethylacridine,
9-[4'-(Isopropylaminocarbonyloxymethyl)anilino]-3,6-dimethoxy-2-methylacridine,
9-[4'-(Isopropylaminocarbonyloxymethyl)anilino]-2,6-dimethoxy-3-methylacridine,
9-[4'-(Isopropylaminocarbonyloxymethyl)anilino]-2,3,6-trimethoxyacridine,
9-[4'-(Isopropylaminocarbonyloxymethyl)anilino]-3-methoxy-2,7-dimethylacridine,
9-[4'-(Isopropylaminocarbonyloxymethyl)anilino]-2-methoxy-3,7-dimethylacridine,
9-[4'-(Isopropylaminocarbonyloxymethyl)anilino]-2,3-methoxy-7-methylacridine,
9-[4'-(Isopropylaminocarbonyloxymethyl)anilino]-2,3,7-trimethylacridine,
9-[4'-(Isopropylaminocarbonyloxymethyl)anilino]-3-methoxy-2,6-dimethylacridine,
9-[4'-(Isopropylaminocarbonyloxymethyl)anilino]-2-methoxy-3,6-dimethylacridine,
9-[4'-(Isopropylaminocarbonyloxymethyl)anilino]-2,3-dimethoxy-6-methylacridine,
9-[4'-(Isopropylaminocarbonyloxymethyl)anilino]-2,3,6-trimethylacridine,
9-[4'-(Isopropylaminocarbonyloxymethyl)anilino]-2,3-dimethoxy-6,7-dimethylacridine,
9-[4'-(Isopropylaminocarbonyloxymethyl)anilino]-2,3,6-trimethoxy-7-methylacridine,
9-[4'-(Isopropylaminocarbonyloxymethyl)anilino]-2,3,7-trimethoxy-6-methylacridine,
9-[4'-(Isopropylaminocarbonyloxymethyl)anilino]-2,3,6,7-tetramethoxyacridine,
9-[4'-(Isopropylaminocarbonyloxymethyl)anilino]-2-methoxy-3,6,7-trimethylacridine,
9-[4'-(Isopropylaminocarbonyloxymethyl)anilino]-3-methoxy-2,6,7-trimethylacridine,
9-[4'-(Isopropylaminocarbonyloxymethyl)anilino]-2,3,6,7-tetramethylacridine,
9-[2'-(β-Methylaminocarbonyloxyethyl)anilino]acridine,
9-[2'-(β-Isopropylaminocarbonyloxyethyl)anilino]acridine,
9-[3'-(β-Methylaminocarbonyloxyethyl)anilino]acridine,
9-[3'-(β-Methylaminocarbonyloxyethyl)anilino]-2-methoxyacridine, 9-[3'-(β-Methylaminocarbonyloxyethyl)anilino]-3-methoxyacridine,
9-[3'-(β-Methylaminocarbonyloxyethyl)anilino]-2-methylacridine,
9-[3'-(β-Methylaminocarbonyloxyethyl)anilino]-3-methylacridine,
9-[3'-(β-Methylaminocarbonyloxyethyl)anilino]-2-methoxy-6-methylacridine,
9-[3'-(β-Methylaminocarbonyloxyethyl)anilino]-2-methoxy-7-methylacridine,
9-[3'-(β-Methylaminocarbonyloxyethyl)anilino]-2,6-dimethoxyacridine,
9-[3'-(β-Methylaminocarbonyloxyethyl)anilino]-2,7-dimethoxyacridine,
9-[3'-(β-Methylaminocarbonyloxyethyl)anilino]-3-methoxy-6-methylacridine,
9-[3'-(β-Methylaminocarbonyloxyethyl)anilino]-6-methoxy-2-methylacridine,
9-[3'-(β-Methylaminocarbonyloxyethyl)anilino]-3,6-dimethoxyacridine,
9-[3'-(β-Methylaminocarbonyloxyethyl)anilino]-2,6-dimethylacridine,
9-[3'-(β-Methylaminocarbonyloxyethyl)anilino]-3,6-dimethylacridine,
9-[3'-(β-Methylaminocarbonyloxyethyl)anilino]-7-methoxy-2,3-dimethylacridine,
9-[3'-(β-Methylaminocarbonyloxyethyl)anilino]-2,6-dimethoxy-7-methylacridine,
9-[3'-(β-Methylaminocarbonyloxyethyl)anilino]-2,7-dimethoxy-3-methylacridine,
9-[3'-(β-Methylaminocarbonyloxyethyl)anilino]-2,3,7-trimethoxyacridine,
9-[3'-(β-Methylaminocarbonyloxyethyl)anilino]-6-methoxy-2,3-dimethylacridine,
9-[3'-(β-Methylaminocarbonyloxyethyl)anilino]-3,6-dimethoxy-2-methylacridine,
9-[3'-(β-Methylaminocarbonyloxyethyl)anilino]-2,3,6-trimethoxyacridine,
9-[3'-(β-Methylaminocarbonyloxyethyl)anilino]-3-methoxy-2,7-dimethylacridine,
9-[3'-(β-Methylaminocarbonyloxyethyl)anilino]-2-methoxy-3,7-dimethylacridine,
9-[3'-(β-Methylaminocarbonyloxyethyl)anilino]-2,3-dimethoxy-7-methylacridine,
9-[3'-(β-Methylaminocarbonyloxyethyl)anilino]-2,3,7-trimethylacridine,
9-[3'-(β-Methylaminocarbonyloxyethyl)anilino]-3-methoxy-2,6-dimethylacridine,
9-[3'-(β-Methylaminocarbonyloxyethyl)anilino]-2-methoxy-3,6-dimethylacridine,
9-[3'-(β-Methylaminocarbonyloxyethyl)anilino]-2,3-dimethoxy-6-methylacridine,
9-[3'-(β-Methylaminocarbonyloxyethyl)anilino]-2,3,6-trimethylacridine,
9-[3'-(β-Methylaminocarbonyloxyethyl)anilino]-2,3-dimethoxy-6,7-dimethylacridine,
9-[3'-(β-Methylaminocarbonyloxyethyl)anilino]-2,3,6-trimethoxy-7-methylacridine,
9-[3'-(β-Methylaminocarbonyloxyethyl)anilino]-2,3,7-trimethoxy-6-methylacridine,
9-[3'-(β-Methylaminocarbonyloxyethyl)anilino]-2,3,6,7-tetramethoxyacridine,
9-[3'-(β-Methylaminocarbonyloxyethyl)anilino]-2-methoxy-3,6,7-trimethylacridine,
9-[3'-(β-Methylaminocarbonyloxyethyl)anilino]-3-methoxy-2,6,7-trimethylacridine,
9-[3'-(β-Methylaminocarbonyloxyethyl)anilino]-2,3,6,7-tetramethylacridine,
9-[3'-(β-Isopropylaminocarbonyloxyethyl)anilino]acridine,
9-[3'-(β-Isopropylaminocarbonyloxyethyl)anilino]-2-methoxyacridine,
9-[3'-(β-Isopropylaminocarbonyloxyethyl)anilino]-3-methoxyacridine,
9-[3'-(β-Isopropylaminocarbonyloxyethyl)anilino]-2-methylacridine,
9-[3'-(β-Isopropylaminocarbonyloxyethyl)anilino]-3-methylacridine,
9-[3'-(β-Isopropylaminocarbonyloxyethyl)anilino]-2-methoxy-6-methylacridine,
9-[3'-(β-Isopropylaminocarbonyloxyethyl)anilino]-2-methoxy-7-methylacridine,
9-[3'-(β-Isopropylaminocarbonyloxyethyl)anilino]-2,6-dimethoxyacridine,
9-[3'-(β-Isopropylaminocarbonyloxyethyl)anilino]-2,7-dimethoxyacridine,
9-[3'-(β-Isopropylaminocarbonyloxyethyl)anilino]-3-methoxy-6-methylacridine,
9-[3'-(β-Isopropylaminocarbonyloxyethyl)anilino]-6-methoxy-2-methylacridine,
9-[3'-(β-Isopropylaminocarbonyloxyethyl)anilino]-3,6-dimethoxyacridine,
9-[3'-(β-Isopropylaminocarbonyloxyethyl)anilino]-2,6-dimethylacridine,
9-[3'-(β-Isopropylaminocarbonyloxyethyl)anilino]-2,7-dimethylacridine,
9-[3'-(β-Isopropylaminocarbonyloxyethyl)anilino]-3,6-dimethylacridine,
9-[3'-(β-Isopropylaminocarbonyloxyethyl)anilino]-7-methoxy-2,3-dimethylacridine,
9-[3'-(β-Isopropylaminocarbonyloxyethyl)anilino]-2,6-dimethoxy-7-dimethylacridine,
9-[3'-(β-Isopropylaminocarbonyloxyethyl)anilino]-2,7-dimethoxy-3-methylacridine,
9-[3'-(β-Isopropylaminocarbonyloxyethyl)anilino]-2,3,6-trimethoxyacridine,
9-[3'-(β-Isopropylaminocarbonyloxyethyl)anilino]-6-methoxy-2,3-dimethylacridine,
9-[3'-(β-Isopropylaminocarbonyloxyethyl)anilino]-3,6-dimethoxy-2-methylacridine,
9-[3'-(β-Isopropylaminocarbonyloxyethyl)anilino]-2,6-dimethoxy-3-methylacridine,
9-[3'-(β-Isopropylaminocarbonyloxyethyl)anilino]-2,3,7-trimethoxyacridine,
9-[3'-(β-Isopropylaminocarbonyloxyethyl)anilino]-3-methoxy-2,7-dimethylacridine,
9-[3'-(β-Isopropylaminocarbonyloxyethyl)anilino]-2-methoxy-3,7-dimethylacridine,
9-[3'-(β-Isopropylaminocarbonyloxyethyl)anilino]-2,3-dimethoxy-7-methylacridine,
9-[3'-(β-Isopropylaminocarbonyloxyethyl)anilino]-2,3,7-trimethylacridine,
9-[3'-(β-Isopropylaminocarbonyloxyethyl)anilino]-3-methoxy-2,6-dimethylacridine,
9-[3'-(β-Isopropylaminocarbonyloxyethyl)anilino]-2-methoxy-3,6-dimethylacridine,
9-[3'-(β-Isopropylaminocarbonyloxyethyl)anilino]-2,3-dimethoxy-6-methylacridine,
9-[3'-(β-Isopropylaminocarbonyloxyethyl)anilino]-2,3,6-trimethylacridine,
9-[3'-(β-Isopropylaminocarbonyloxyethyl)anilino]-2,3-dimethoxy-6,7-dimethylacridine,
9-[3'-(β-Isopropylaminocarbonyloxyethyl)anilino]-2,3,6-trimethoxy-7-methylacridine,
9-[3'-(β-Isopropylaminocarbonyloxyethyl)anilino]-2,3,7-trimethoxy-6-methylacridine, 9-[3'-(β-Isopropylaminocarbonyloxyethyl)anilino]-2,3,6,7-tetramethoxyacridine,
9-[3'-(β-Isopropylaminocarbonyloxyethyl)anilino]-2-methoxy-3,6,7-trimethylacridine,
9-[3'-(β-Isopropylaminocarbonyloxyethyl)anilino]-3-methoxy-2,6,7-trimethylacridine,
9-[3'-(β-Isopropylaminocarbonyloxyethyl)anilino]-2,3,6,7-tetramethylacridine,
9-[4'-(β-Methylaminocarbonyloxyethyl)anilino]acridine,
9-[4'-(β-Methylaminocarbonyloxyethyl)anilino]-2-methoxyacridine,
9-[4'-(β-Methylaminocarbonyloxyethyl)anilino]-3-methoxyacridine,
9-[4'-(β-Methylaminocarbonyloxyethyl)anilino]-2-methylacridine,
9-[4'-(β-Methylaminocarbonyloxyethyl)anilino]-3-methylacridine,
9-[4'-(β-Methylaminocarbonyloxyethyl)anilino]-2-methoxy-6-methylacridine,
9-[4'-(β-Methylaminocarbonyloxyethyl)anilino]-2-methoxy-7-methylacridine,
9-[4'-(β-Methylaminocarbonyloxyethyl)anilino]-2,6-dimethoxyacridine,
9-[4'-(β-Methylaminocarbonyloxyethyl)anilino]-2,7-dimethoxyacridine,
9-[4'-(β-Methylaminocarbonyloxyethyl)anilino]-3-methoxy-6-methylacridine,
9-[4'-(β-Methylaminocarbonyloxyethyl)anilino]-6-methoxy-2-methylacridine,
9-[4'-(β-Methylaminocarbonyloxyethyl)anilino]-3,6-dimethoxyacridine,
9-[4'-(β-Methylaminocarbonyloxyethyl)anilino]-2,6-dimethylacridine,
9-[4'-(β-Methylaminocarbonyloxyethyl)anilino]-2,7-dimethylacridine,
9-[4'-(β-Methylaminocarbonyloxyethyl)anilino]-3,6-dimethylacridine,
9-[4'-(β-Methylaminocarbonyloxyethyl)anilino]-2,6-dimethoxy-7-methylacridine,
9-[4'-(β-Methylaminocarbonyloxyethyl)anilino]-2,7-dimethoxy-3-methylacridine,
9-[4'-(β-Methylaminocarbonyloxyethyl)anilino]-2,3,7-trimethoxyacridine,
9-[4'-(β-Methylaminocarbonyloxyethyl)anilino]-6-methoxy-2,3-dimethylacridine,
9-[4'-(β-Methylaminocarbonyloxyethyl)anilino]-3,6-dimethoxy-2-methylacridine,
9-[4'-(β-Methylaminocarbonyloxyethyl)anilino]-2,6-dimethoxy-3-methylacridine,
9-[4'-(β-Methylaminocarbonyloxyethyl)anilino]-2,3,6-trimethoxyacridine,
9-[4'-(β-Methylaminocarbonyloxyethyl)anilino]-3-methoxy-2,7-dimethylacridine,
9-[4'-(β-Methylaminocarbonyloxyethyl)anilino]-2-methoxy-3,7-dimethylacridine,
9-[4'-(β-Methylaminocarbonyloxyethyl)anilino]-2,3-dimethoxy-7-methylacridine,
9-[4'-(β-Methylaminocarbonyloxyethyl)anilino]-2,3,7-trimethylacridine,
9-[4'-(β-Methylaminocarbonyloxyethyl)anilino]-3-methoxy-2,6-dimethylacridine,
9-[4'-(β-Methylaminocarbonyloxyethyl)anilino]-2-methoxy-3,6-dimethylacridine,
9-[4'-(β-Methylaminocarbonyloxyethyl)anilino]-2,3-dimethoxy-6-methylacridine,
9-[4'-(β-Methylaminocarbonyloxyethyl)anilino]-2,3,6-trimethylacridine,
9-[4'-(β-Methylaminocarbonyloxyethyl)anilino]-2,3-dimethoxy-6,7-dimethylacridine,
9-[4'-(β-Methylaminocarbonyloxyethyl)anilino]-2,3,6-trimethoxy-7-methylacridine,
9-[4'-(β-Methylaminocarbonyloxyethyl)anilino]-2,3,7-trimethoxy-6-methylacridine,
9-[4'-(β-Methylaminocarbonyloxyethyl)anilino]-2,3,6,7-tetramethoxyacridine,
9-[4'-(β-Methylaminocarbonyloxyethyl)anilino]-2-methoxy-3,6,7-trimethylacridine,
9-[4'-(β-Methylaminocarbonyloxyethyl)anilino]-3-methoxy-2,6,7-trimethylacridine,
9-[4'-(β-Methylaminocarbonyloxyethyl)anilino]-2,3,6,7-tetramethylacridine,
9-[4'-(β-Isopropylaminocarbonyloxyethyl)anilino]acridine,
9-[4'-(β-Isopropylaminocarbonyloxyethyl)anilino]-2-methoxyacridine,
9-[4'-(β-Isopropylaminocarbonyloxyethyl)anilino]-3-methoxyacridine,
9-[4'-(β-Isopropylaminocarbonyloxyethyl)anilino]-2-methylacridine,
9-[4'-(β-Isopropylaminocarbonyloxyethyl)anilino]-3-methylacridine,
9-[4'-(β-Isopropylaminocarbonyloxyethyl)anilino]-2-methoxy-6-methylacridine,
9-[4'-(β-Isopropylaminocarbonyloxyethyl)anilino]-2-methoxy-7-methylacridine,
9-[4'-(β-Isopropylaminocarbonyloxyethyl)anilino]-2,6-dimethoxyacridine,
9-[4'-(β-Isopropylaminocarbonyloxyethyl)anilino]-2,7-dimethoxyacridine,
9-[4'-(β-Isopropylaminocarbonyloxyethyl)anilino]-3-methoxy-6-methylacridine,
9-[4'-(β-Isopropylaminocarbonyloxyethyl)anilino]-6-methoxy-2-methylacridine,
9-[4'-(β-Isopropylaminocarbonyloxyethyl)anilino]-3,6-dimethoxyacridine,
9-[4'-(β-Isopropylaminocarbonyloxyethyl)anilino]-2,6-dimethylacridine,
9-[4'-(β-Isopropylaminocarbonyloxyethyl)anilino]-2,7-dimethylacridine,
9-[4'-(β-Isopropylaminocarbonyloxyethyl)anilino]-3,6-dimethylacridine,
9-[4'-(β-Isopropylaminocarbonyloxyethyl)anilino]-7-methoxy-2,3-dimethylacridine,
9-[4'-(β-Isopropylaminocarbonyloxyethyl)anilino]-2,6-dimethoxy-7-methylacridine,
9-[4'-(β-Isopropylaminocarbonyloxyethyl)anilino]-2,7-dimethoxy-3-methylacridine,
9-[4'-(β-Isopropylaminocarbonyloxyethyl)anilino]-2,3,7-trimethoxyacridine,
9-[4'-(β-Isopropylaminocarbonyloxyethyl)anilino]-6-methoxy-2,3-dimethylacridine,
9-[4'-(β-Isopropylaminocarbonyloxyethyl)anilino]-3,6-dimethoxy-2-methylacridine,
9-[4'-(β-Isopropylaminocarbonyloxyethyl)anilino]-2,6-dimethoxy-3-methylacridine,
9-[4'-(β-Isopropylaminocarbonyloxyethyl)anilino]-2,3,6-trimethoxyacridine,
9-[4'-(β-Isopropylaminocarbonyloxyethyl)anilino]-3-methoxy-2,7-dimethylacridine,
9-[4'-(β-Isopropylaminocarbonyloxyethyl)anilino]-2-methoxy-5,7-dimethylacridine,
9-[4'-(β-Isopropylaminocarbonyloxyethyl)anilino]-2,3-dimethoxy-7-methylacridine,
9-[4'-(β-Isopropylaminocarbonyloxyethyl)anilino]-2,3,7-trimethylacridine, 9-[4'-(β-Isopropylaminocarbonyloxyethyl)anilino]-3-methoxy-2,6-dimethylacridine,
9-[4'-(β-Isopropylaminocarbonyloxyethyl)anilino]-2-methoxy-3,6-dimethylacridine,
9-[4'-(β-Isopropylaminocarbonyloxyethyl)anilino]-2,3-dimethoxy-6-methylacridine,
9-[4'-(β-Isopropylaminocarbonyloxyethyl)anilino]-2,3,6-trimethylacridine,
9-[4'-(β-Isopropylaminocarbonyloxyethyl)anilino]-2,3-dimethoxy-6,7-dimethylacridine,
9-[4'-(β-Isopropylaminocarbonyloxyethyl)anilino]-2,3,6-trimethoxy-7-methylacridine,
9-[4'-(β-Isopropylaminocarbonyloxyethyl)anilino]-2,3,7-trimethoxy-6-methylacridine,
9-[4'-(β-Isopropylaminocarbonyloxyethyl)anilino]-2,3,6,7-tetramethoxyacridine,
9-[4'-(β-Isopropylaminocarbonyloxyethyl)anilino]-2-methoxy-3,6,7-trimethylacridine,
9-[4'-(β-Isopropylaminocarbonyloxyethyl)anilino]-3-methoxy-2,6,7-trimethylacridine,
9-[4'-(β-Isopropylaminocarbonyloxyethyl)anilino]-2,3,6,7-tetramethylacridine, The subject invention also provides a method of synthesizing a compound having the structure:

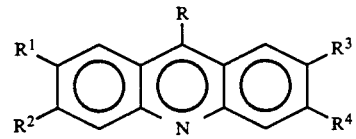

wherein each of $R^1$, $R^2$, $R^3$, $R^4$, are the same or different and are hydrogen (H), or a lower alkyl group of from 1-4 carbon atoms, or a lower alkoxy group of from about 1-4 carbon atoms. R is a substituted aniline

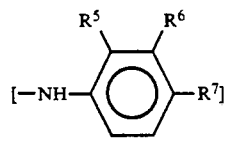

wherein one of $R^5$, $R^6$, $R^7$ is an alkanol having the formula $-(CH_2)_nOH$, $n=1-4$, or its carbamate ester having the formula $-(CH_2)_nOCONR'R''$, $n=1-4$, and wherein R' and R'' the same or different lower alkyl groups of from about 1 to 4 carbon atoms, such as methyl, ethyl, n-propyl or i-propyl, one of R' and R'' may be hydrogen (H), and the remaining groups are hydrogen.
which comprises:
a) contacting a compound having the structure:

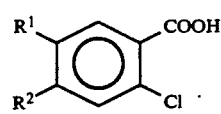

wherein each of $R^1$ and $R^2$ are the same or different and are hydrogen, or a lower alkyl group of from about 1-4 carbon atoms or a lower alkoxy group of from about 1-4 carbon atoms, $R^1$ and $R^2$ are as herein defined throughout this synthesis;
with a compound having the structure:

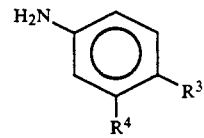

wherein each of $R^3$ and $R^4$ are the same or different and are hydrogen, or a lower alkyl group of from about 1-4 carbon atoms or a lower alkoxy group of from about 1-4 carbon atoms; $R^3$ and $R^4$ are as herein defined throughout this synthesis; under such conditions so as to form a compound having the structure:

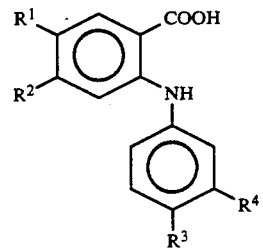

b) treating the compound formed in step (a) under such conditions so as to form a compound having the structure:

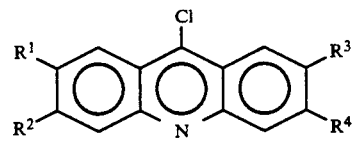

or under such conditions so as to form a compound having the structure:

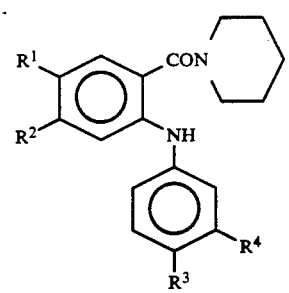

c) if the compound formed in step (b) is a compound having the structure:

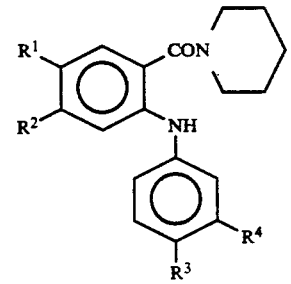

then treating the compound under such conditions so as to form the compound having the structure:

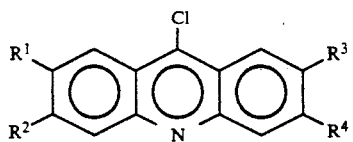

d) condensing the compound formed in either step (b) or step (c) having the structure:

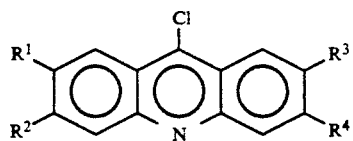

under such conditions so as to form a compound having the structure:

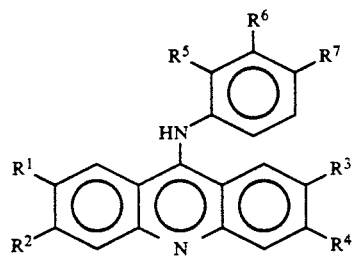

wherein each of $R^1$, $R^2$, $R^3$, $R^4$, are as previously defined, and wherein one of $R^5$, $R^6$, $R^7$ is an alkanol having the formula $-(CH_2)_nOH$, n=1–4, and the others are hydrogen;

e) treating the compound formed in step (d) under such conditions so as to form a compound having the structure:

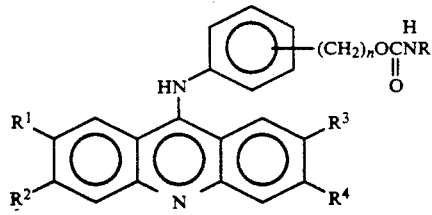

In the preferred embodiment, in step (a) the contacting comprises condensing in the presence of copper, cuprous oxide, and base, and preferably the base is potassium carbonate or sodium carbonate. It is also preferred that in step (a) the contacting is effected in a solvent.

Preferred solvents include, but are not limited to, 2-ethoxyethanol, glyme, N,N-dimethylformamide, or acetamide. The contacting of step (a) is preferably performed at a temperature range of from about 60° C. to 200° C., and must preferably at about 140° C.

In the preferred embodiment in step (b) the treating comprises contacting the compound formed in step (a) with triphenylphosphine and bromotrichloromethane, and preferably the treating is effected in a solvent. Preferred solvents include, but are not limited to tetrahydrofuran or dioxan.

The treating of step (b) is best perfomed at a temperature range of from about 36° C. to 145° C., with the most preferred conditions being at about 66° C., for about 1 to 8 hours.

In step (b) the treating comprises contacting the compound formed in step (a) with phosphorus oxychloride. It is also preferred that in step (c) the treating comprises contacting the compound formed in step (b) with phosphorus oxychloride.

In the preferred embodiment in step (d) the condensing comprises contacting the compound having the structure:

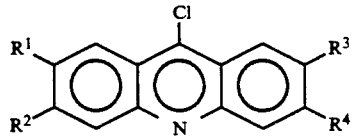

wherein each of $R^1$, $R^2$, $R^3$, $R^4$, are the same or different and are hydrogen (H), or a lower alkyl group of from about 1–4 carbon atoms, or a lower alkoxy group of from about 1–4 carbon atoms;
with a substituted aniline having the structure:

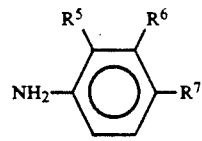

wherein one of $R^5$, $R^6$, $R^7$, is an alkanol having the formula $-(CH_2)_nOH$, n=1–4, and the others are hydrogen.

Preferrably in step (d) the condensing is effected in the presence of an acid catalyst. Preferred acid catalysts includes, but are not limited to, methylsufonic acid, toluenesulfonic acid, benzene sulfonic acid, or camphorsulfonic acid.

The acid catalyst can be a Lewis acid, with the preferred Lewis acid being boron trihalide.

It is preferred that in step (d) the condensing is effected in an inert solvent such as a chlorohydrocarbon, and more preferrably the chlorohydrocarbon is methylene chloride, chloroform, ethylene dichloride, or ethylene tetrachloride.

Another preferred inert solvent is an ether, preferrably tetrahydrofuran, dioxan, or diethyl ether.

In the preferred embodiment in step (e) the treating comprises contacting the compound formed in step (d) with an alkylisocyanate in the presence of an organic amine. Preferred organic amines include, but are not limited to, trimethylamine, triethylamine, N,N-dimethylaniline, 4-dimethylamino pyridine, 1,5-diazabicyclo[4.3.0]non-5-ene, or 1,8-diaza bicyclo [5.4.0]undec-7-ene.

In the preferred embodiment in step (e) the treating is effected in a solvent, preferrably a halogenated hydrocarbon. Preferred halogenated hydrocarbons include, but are not limited to, methylene chloride, chloroform, or dichloroethane.

Preferrably, in step (e) the treating is performed at a temperature range of form about 0° C. to 120° C., and most preferrably at about 25° C., wherein the treating is performed for about 1 hour to 5 days.

The subject invention also provides a compound having the structure:

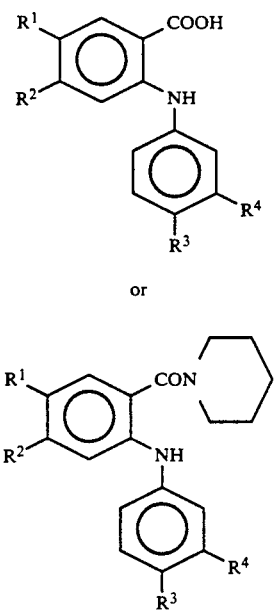

wherein each of $R^1$, $R^2$, $R^3$, $R^4$, are the same or different and are hydrogen, or lower alkyl groups of from about 1-4 carbon atoms, or lower alkoxy groups of from about 1-4 carbon atoms.

Some of these compound may be selected from the group consisting of:
N-(m-Tolyl)-5-methoxyanthranilopiperide,
N-(m-Tolyl)-4-methoxyanthranilopiperide,
N-(m-Tolyl)-5-methylanthranilopiperide,
N-(m-Tolyl)-4-methylanthranilopiperide,
N-(p-Tolyl)-5-methoxyanthranilopiperide,
N-(p-Tolyl)-4-methoxyanthranilopiperide,
N-(p-Tolyl)-5-methylanthranilopiperide,
N-(p-Tolyl)-4-methylanthranilopiperide,
N-(m-Anisyl)-5-methoxyanthranilopiperide,
N-(m-Anisyl)-4-methoxyanthranilopiperide,
N-(m-Anisyl)-5-methylanthranilopiperide,
N-(m-Anisyl)-4-methylanthranilopiperide,
N-(p-Anisyl)-5-methoxyanthranilopiperide,
N-(p-Anisyl)-4-methoxyanthranilopiperide,
N-(p-Anisyl)-5-methylanthranilopiperide,
N-(p-Anisyl)-4-methylanthranilopiperide.

The subject invention further provides a compound having the structure:

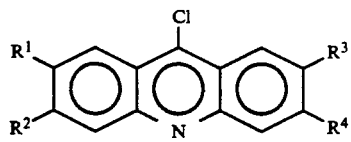

wherein each of $R^1$, $R^2$, $R^3$, $R^4$ are the same or different and are hydrogen, or a lower alkyl group of from about 1-4 carbon atoms, or a lower alkoxy group of from about 1-4 carbon atoms.

This compound may be selected from the group consisting of, but not limited to:

9-Chloro-2,6-dimethoxyacridine,
9-Chloro-3-methoxy-6-methylacridine,
9-Chloro-6-methoxy-2-methylacridine,
9-Chloro-2,6-dimethylacridine,
9-Chloro-2,7-dimethylacridine,
9-Chloro-3,6-dimethylacridine,
9-Chloro-7-methoxy-2,3-dimethylacridine,
9-Chloro-3,7-dimethoxy-2-methylacridine,
9-Chloro-2,7-dimethoxy-3-methylacridine,
9-Chloro-2,3,7-trimethoxyacridine,
9-Chloro-6-methoxy-2,3-dimethylacridine,
9-Chloro-3,6-dimethoxy-2-methylacridine,
9-Chloro-2,6-dimethoxy-3-methylacridine,
9-Chloro-2,3,6-trimethoxyacridine,
9-Chloro-3-methoxy-2,7-dimethylacridine,
9-Chloro-2-methoxy-3,7-dimethylacridine,
9-Chloro-2,3-dimethoxy-7-methylacridine,
9-Chloro-2,3,7-trimethylacridine,
9-Chloro-3-methoxy-2,6-dimethylacridine,
9-Chloro-2-methoxy-3,6-dimethylacridine,
9-Chloro-2,3-dimethoxy-6-methylacridine,
9-Chloro-2,3,7-trimethylacridine,
9-Chloro-2,3-dimethoxy-6,7-dimethylacridine,
9-Chloro-2,3,6-trimethoxy-7-methylacridine,
9-Chloro-2,3,7-trimethoxy-6-methylacridine,
9-Chloro-2,3,6,7-tetramethoxyacridine,
9-Chloro-2-methoxy-3,6,7-trimethylacridine,
9-Chloro-3-methoxy-2,6,7-trimethylacridine,
9-Chloro-2,3,6,7-tetramethylacridine.

The subject invention also provides a pharmaceutical composition comprising an amount of the compound of formula I or a salt thereof, effective to inhibit the growth of tumor cells and a physiologically acceptable carrier. In the preferred embodiment, the pharmaceutical composition kills the tumor cells.

Physiologically acceptable carriers, as discussed throughout the application, are to include any carrier compatible with life. The choice of carrier is readily determinable to one skilled in art. The physiologically acceptable carrier encompasses any of the standard carriers such as sterile solutions, tablets, coated tablets and capsules. Typically such carriers contain excipients such as starch, milk, sugar, certain types of clay, gelatin, stearic acid, talc, vegetable fats or oils, gums glycols, or other known excipients. Such carriers may also include flavor and color additives or other ingredients. Compositions comprising such carriers are formulated by well known conventional methods. However a composition comprising a compound of the subject invention effective to inhibit growth of tumor cells is previously unknown.

The subject invention also provides a method of treating a subject having a tumor which comprises administering to the subject an amount of a composition described above effective to inhibit the growth of tumor cells. The method of treatment may be either in response to a diagnosed tumor or as a prophylactic measure designed to prevent the growth of tumor cells. It is preferred that the inhibition of tumor cell growth results ultimately in the death of the tumor cells.

In addition, the administration of the composition may be effected by any of the well known methods, including but limited to, oral, intravenous, intramuscular, and subcutaneous administration.

In the practice of this method, the amount of the compound of formula I incorporated in the composition may vary widely. Methods for determining the precise amount are well known to those skilled in the art and depend inter alia upon the subject being treated, the specific pharmaceutical carrier and route of administration being employed, and the frequency with which the composition is to be administered.

Lastly, the subject invention provides, a method of inhibiting the growth of tumor cells which comprises contacting the cells with an amount of a compound of formula I effective to inhibit the growth of tumor cells Once again, it is preferred that the inhibition of tumor cell growth results in the killing of the tumor cells.

Experimental Detail

The present invention relates to the novel class of acridines which contain a covalent bond forming capability. Such compounds may intercalate into DNA and then bind covalently to DNA thereby exerting cytotoxic activity. The mechanism(s) of biological action of the compounds incorporated into this invention are different than that of the known acridine anticancer agents, such as amsacrin, which appears to induce DNA cleavage mediated by topoisomerse II [E. M. Nelson et al., Proc. Nat. Acad. Sci., U.S.A., 81:1361 (1984); Y. Pommier et al., Biochemistry, 23:3194 (1984)], but the intercalation of amsacrin into DNA is reversible [W. A. Denny and L. P. G. Wakelin, Cancer Res., 46:1717 (1986)]. Compounds of the present invention are so designed that they intercalate into DNA and irreversibly bind to DNA through covalent bound formation between the agents and DNA.

The starting materials for the process of the present invention can be subsumed under formula II as below:

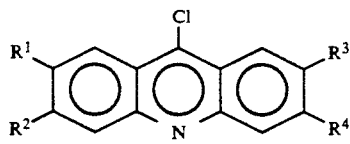

wherein each of $R^1$, $R^2$, $R^3$, and $R^4$, are the same or different and are hydrogen (H), lower alkyl groups of 1-4 carbon atoms, such as methyl (Me), ethyl (Et), or propyl (Pr) groups, or lower alkoxy groups of 1-4 carbon atoms such as methoxy (MeO), ethoxy (EtO), or propoxy (PrO) groups.

Figure 2:
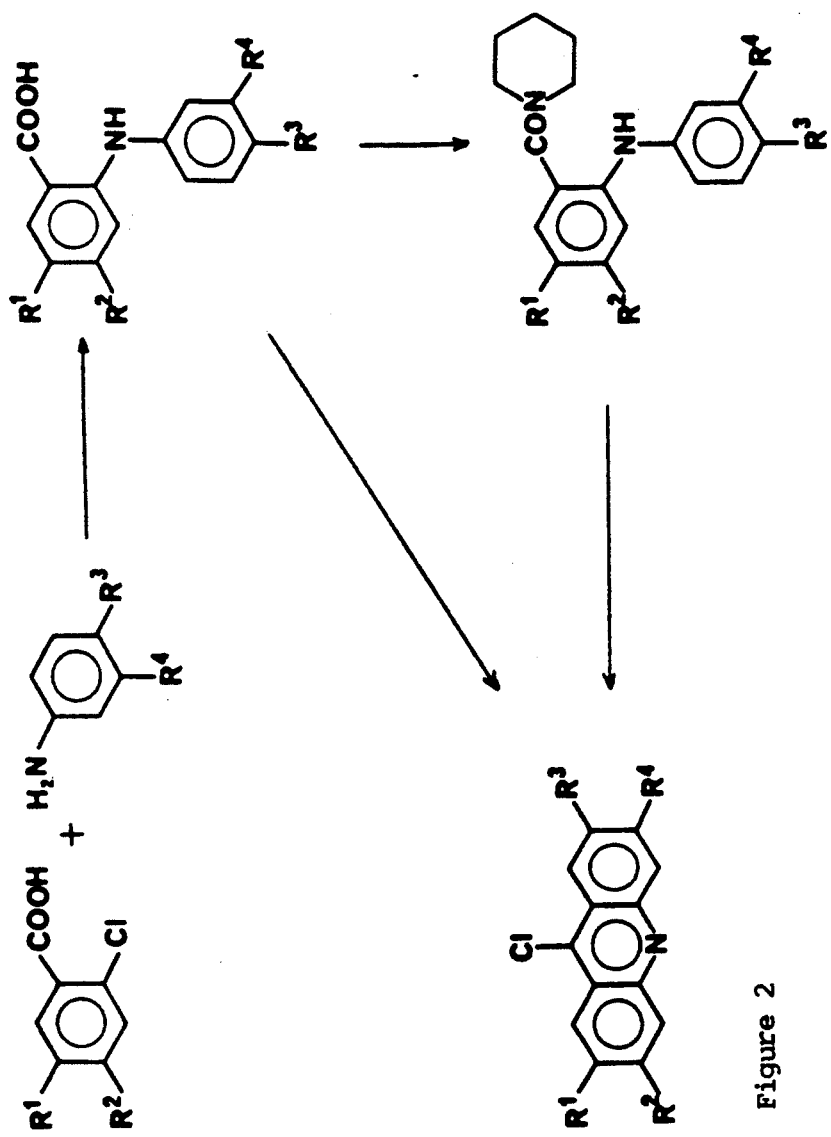
FIG. 2: Synthesis of 9-chloroacridine derivatives from o-chlorobenzoic acid and substituted aniline.

Compounds of formula II are prepared in two or three steps from substituted o-chlorobenzoic acid (1) and substituted aniline (2) as outlined in FIG. 2.

Compounds 1 and 2 are condensed to diphenylamine derivatives (3) in the presence of copper, cuprous oxide and base, such as potassium carbonate or sodium carbonate, in a solvent, such as 2-ethoxyethanol, glyme, N,N-dimethylformamide, acetamide, at a temperature range of about 60° C. to 200° C., preferably at 140° C. for a period of from 1 to 5 hours.

Typical examples of 3 are listed in the following Table 1.

TABLE 1

| Compound | $R^1$ | $R^2$ | $R^3$ | $R^4$ | mp (°C.) |
|---|---|---|---|---|---|
| 3a | MeO | H | Me | H | 160-161 |
| 3b | MeO | H | MeO | Me | 146-147 |
| 3c | MeO | H | MeO | H | 138-138.5 |
| 3d | MeO | H | H | MeO | 157-159 |

Compounds 3 are then converted into the correspondng piperides 4 in the present of triphenylphosphine and bromotrichloromethane in a solvent such as tetrahydrofuran, dioxan, or the like, at a temperature range of from 36° C. to 145° C., preferably at 66° C. for a period of from 1 to 8 hours. Treatment of piperides 4 with phosphorus oxychloride affords the corresponding 9-chloroacridines having formula II. The latter can also be prepared directly from 3 by phosphorous oxychloride treatment.

New compounds of structure 4 are listed in Table 2.

TABLE 2

| Compound | $R^1$ | $R^2$ | $R^3$ | $R^4$ | mp (°C.) |
|---|---|---|---|---|---|
| 4a | MeO | H | Me | H | syrup |
| 4b | MeO | H | MeO | H | syrup |
| 4c | H | H | Me | H | 78-79.5 |
| 4d | H | H | MeO | H8 | 93-94 |

Some examples of new 9-chloroacridine derivatives of formula II are listed in Table 3.

TABLE 3

| Compound | $R^1$ | $R^2$ | $R^3$ | $R^4$ | mp (°C.) |
|---|---|---|---|---|---|
| IIa | MeO | H | Me | H | 158-159 |
| IIb | MeO | H | H | Me | 163-164.5 |
| IIc | MeO | H | MeO | H | 195-196 |

Compounds of formula II are condensed with substituted anilines in the presence of an acid catalyst such as methylsulfonic acid, toluenesulfonic acid, benzenesulfonic acid, camphorsulfonic acid, and boron trihalide or other Lewis acid, in an inert solvent such as a chlorohydrocarbon, including methylene chloride, chloroform, ethylene dichloride, and ethylene tetrachloride, or an ether, including tetrahydrofuran, dioxan, and diethylether under reflux for about 1 to 5 hours.

The products of the above condensation can be represented by formula III below.

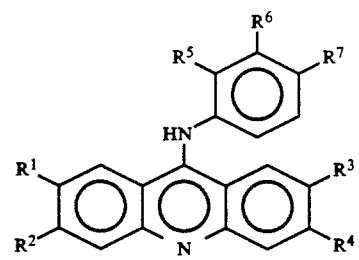

wherein each of $R^1$, $R^2$, $R^3$, $R^4$, are the same or different and are hydrogen (H), lower alkyl groups of 1-4 carbon atoms, such as methyl (Me), ethyl (Et) or propyl (Pr) groups, or lower alkoxy groups of 1-4 carbon atoms, such as methoxy (MeO), ethoxy (EtO) or propoxy (PrO) groups.

One of $R^5$, $R^6$, $R^7$, is an hydroxyalkyl group [—($CH_2$)$_n$OH, n=1-4], such as hydroxymethyl, hydroxyethyl, hydroxypropyl and hydroxybutyl, and the rest are hydrogen.

Typical examples of formula III are listed in Table 4.

TABLE 4

| Compd. | R¹ | R² | R³ | R⁴ | R⁵ | R⁶ | R⁷ | mp (°C.) |
|---|---|---|---|---|---|---|---|---|
| IIIa | H | H | H | H | CH₂OH | H | H | 245 (dec) |
| IIIb | H | H | H | H | H | CH₂OH | H | 230–232 |
| IIIc | H | H | H | H | H | H | CH₂OH | >275 |
| IIId | H | H | H | H | (CH₂)₂OH | H | H | 219–220 |
| IIIe | H | H | H | H | H | (CH₂)₂OH | H | 135–137 |
| IIIf | H | H | H | H | H | H | (CH₂)₂OH | 252—252 |
| IIIg | H | H | Me | H | H | CH₂OH | H | 200–201 (dec) |
| IIIh | H | H | H | Me | H | CH₂OH | H | 163–165 |
| IIIi | H | H | MeO | H | H | CH₂OH | H | 221–223 |
| IIIj | H | H | H | MeO | H | CH₂OH | H | 99–101 (dec) |
| IIIk | MeO | H | Me | H | H | CH₂OH | H | 191–193 |
| IIIl | MeO | H | H | Me | H | CH₂OH | H | 225–227 (dec) |
| IIIm | MeO | H | MeO | H | H | CH₂OH | H | 237–238 |
| IIIn | H | H | MeO | H | H | (CH₂)₂OH | H | 186–188 |
| IIIo | H | H | Me | H | H | H | CH₂OH | 267–268 (dec) |
| IIIp | H | H | H | Me | H | H | CH₂OH | 213–214 (dec) |
| IIIq | H | H | MeO | H | H | H | CH₂OH | 215–217 |
| IIIr | H | H | H | MeO | H | H | CH₂OH | 150–151 |
| IIIs | MeO | H | Me | H | H | H | CH₂OH | 242–244 (dec) |
| IIIt | MeO | H | H | Me | H | H | CH₂OH | 232–235 (dec) |
| IIIu | MeO | H | MeO | H | H | H | CH₂OH | 248–249 (dec) |
| IIIv | H | H | H | MeO | H | H | (CH₂)₂OH | 192–193 (dec) |
| IIIw | MeO | H | MeO | H | H | H | (CH₂)₂OH | 175–176 |

Treatment of compounds of formula III with alkylisocyanate in the presence of an organic amine such as trimethylamine, triethylamine, N,N-dimethylaniline, 4-dimethylaminopyridine, 1,5-diazabicyclo[4,3,0]non-5-ene or 1,8-diazabicyclo[5,4,0]undec-7-ene or the like in a solvent such as an halogenated hydrocarbon such as methylene chloride, chloroform, dichloroethane or the like at a temperature range of from 0° C. to 120° C., preferably at 25° C. for a period of from 1 hour to 5 days affords the corresponding carbamate esters of formula IV shown below:

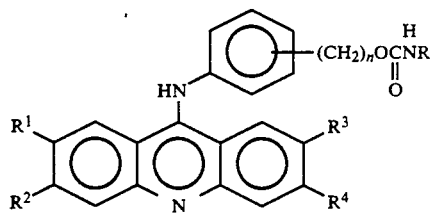

Typical examples of carbamate derivatives with formula IV are listed in Table 5.

TABLE 5

| Compd. | R¹ | R² | R³ | R⁴ | position of side chain | n | R | mp (°C.) |
|---|---|---|---|---|---|---|---|---|
| IVa | H | H | H | H | 2' | 1 | Me | 167–168 |
| IVb | H | H | H | H | 2' | 1 | i-Pr | 155–156 (dec) |
| IVc | H | H | H | H | 3' | 1 | Me | 143–145 |
| IVd | H | H | H | H | 3' | 1 | i-Pr | 73–74 |
| IVe | H | H | H | H | 4' | 1 | Me | 165–166 (dec) |
| IVf | H | H | H | H | 4' | 1 | i-Pr | 139–140 (dec) |
| IVg | H | H | H | H | 3' | 2 | Me | 73–74 |
| IVh | H | H | H | H | 3' | 2 | i-Pr | 168–170 |
| IVi | H | H | H | H | 4' | 2 | Me | 84–85 |
| IVj | H | H | H | H | 4' | 2 | i-Pr | 66–67 |
| IVk | H | MeO | H | H | 3' | 1 | Me | 65–66 |
| IVl | H | MeO | H | H | 3' | 1 | i-Pr | 94–96 |
| IVm | MeO | H | MeO | H | 3' | 1 | Me | 193–195 |
| IVn | MeO | H | MeO | H | 3' | 1 | i-Pr | 148–149 |
| IVo | MeO | H | MeO | H | 4' | 1 | Me | 160–161 |
| IVp | MeO | H | MeO | H | 4' | 1 | i-Pr | 119–121 |
| IVq | MeO | H | MeO | H | 4' | 2 | Me | 153–155 |

TABLE 5-continued

| Compd. | R¹ | R² | R³ | R⁴ | position of side chain | n | R | mp (°C.) |
|---|---|---|---|---|---|---|---|---|
| IVq | MeO | H | MeO | H | 4' | 2 | i-Pr | 125–126 |

The following examples are illustrative of the process and products of the present invention, but are not to be construed as limiting.

Example 1

A mixture of 2-chloro-5-methoxybenzoic acid (14.0 g, 80.0 mmol), potassium carbonate (13.8 g, mol), powdered copper (1.5 g), cuprous oxide (1.5 g), and p-toluidine (9.4 g, 88.0 mmol) in 2-ethoxyethanol (120 ml) is heated at 140° C. for 3 hours. After cooling, the dark mixture is acidified to about pH 2 with 1N hydrochloric acid, and then diluted with water (600 ml). The solid precipitates are collected by filtration, dissolved in hot 10% sodium carbonate solution, charcoaled, and filtered through a Celite bed. The filtrate is acidified with concentrated hydrochloric acid to about pH 2, and the mixture is extracted with ethyl ether (5×100 ml). The combined extracts are washed with 1N hydrochloric acid (200 ml) and water (2×200 ml), dried over sodium sulfate, concentrated in vacuo, and the solid residue is recrystallized from ethanol-water to give N-(p-tolyl)-5-methoxyanthranilic acid (13.9 g, 68% yield), mp 160°–161° C.

Microanalyses. Caluclated for $C_{15}H_{15}NO_3$: C, 70.02; H, 5.88; N, 5.44%. Found: C, 69.87; H, 5.92; N, 5.42%.

By following the same procedure but using the corresponding 2-chlorobenzoic acids and substituted anilines, the following derivatives of anthranilic acid are prepared:

N-(m-Tolyl)-5-methoxyanthranilic acid,
N-(m-Tolyl)-4-methoxyanthranilic acid,
N-(m-Tolyl)-5-methylanthranilic acid,
N-(m-Tolyl)-4-methylanthranilic acid,
N-(p-Tolyl)-4-methoxyanthranilic acid,
N-(p-Tolyl)-5-methylanthranilic acid,
N-(p-Tolyl)-4-methylanthranilic acid,
N-(m-Anisyl)-5-methoxyanthranilic acid,
N-(m-Anisyl)-4-methoxyanthranilic acid, N-(m-Anisyl)-5-methylanthranilic acid,
N-(m-Anisyl)-4-methylanthranilic acid,
N-(p-Anisyl)-5-methoxyanthranilic acid,
N-(p-Anisyl)-4-methoxyanthranilic acid,
N-(p-Anisyl)-5-methylanthranilic acid,
N-(p-Anisyl)-4-methylanthranilic acid.

Example 2

A mixture of N-(m-tolyl)-5-methoxyanthranilic acid (7.71 g 30 mmol), triphenylphosphine (9.45 g, 36 mmol), bromotrichloromethane (7.38 ml, 75 mmol) and piperidine (13.4 mL, 135 mmol) in tetrahydrofuran (120 ml) is heated for 2 hours under reflux with stirring. The mixture is poured on to ice (100 g), extracted with dichloromethane (3×100 ml). The combined extracts are washed with water (4×100 ml), dried over sodium sulfate, concentrated in vacuo, and the residue chromatographed on a silica gel column using n-hexaneethylacetate (2:1)as the eluent to give N-(m-tolyl)-5-methoxyanthranilopiperide as a brown syrup (8.69 g, 89%).

Microanalyses. Calculated for $C_{20}H_{24}N_2O_2$: C, 74.05; H, 7.46; N, 8.83%, Found C: 73.91; H, 7.58; N, 8.51%

By using the same procedure but using the corresponding N-(substituted-phenyl)anthranilic acid derivatives, the following piperides are synthesized:
N-(m-Tolyl)-4-methoxyanthranilopiperide,
N-(m-Tolyl)-5-methylanthranilopiperide,
N-(m-Tolyl)-4-methylanthranilopiperide,
N-(p-Tolyl)-5-methoxyanthranilopiperide,
N-(p-Tolyl)-4-methoxyanthranilopiperide,
N-(p-Tolyl)-5-methylanthranilopiperide,
N-(p-Tolyl)-4-methylanthranilopiperide,
N-(m-Anisyl)-5-methoxyanthranilopiperide,
N-(m-Anisyl)-4-methoxyanthranilopiperide,
N-(m-Anisyl)-5-methylanthranilopiperide,
N-(p-Anisyl)-4-methylanthranilopiperide,
N-(p-Anisyl)-5-methoxyanthranilopiperide,
N-(p-Anisyl)-4-methoxyanthranilopiperide,
N-(p-Anisyl)-5-methylanthranilopiperide,
N-(p-Anisyl)-4-methylanthranilopiperide.

Example 3

N-(m-Tolyl)anthranilopiperide (32 g, 0.11 mol) is dissolved in phophorus oxychloride (150 ml), and the solution is heated at 150° C. for 4 hours, and then excess phosphorus oxychloride is removed in vacuo. To the residue is added water (500 ml) followed by aqueous ammonia (200 ml). The mixture is extracted with chloroform (3×500 ml). The combined extracts are washed with water (3×11), dried over sodium sulfate, concentrated in vacuo, and the residue chromatographed over a silica gel column using commercial chloroform as the eluent to give 9-chloro-3-mehtylacridine, (22.4 g, 90%) as brown solid, mp 117°–118° C.

By following the same procedure but using the correponding anthranilopiperides, the following 9-chloroacridines are prepared:
9-Chloro-2,6-dimethoxyacridine,
9-Chloro-3-methoxy-6-methylacridine,
9-Chloro-6-methoxy-2-methylacridine,
9-Chloro-2,6-dimethylacridine,
9-Chloro-2,7-dimethylacridine,
9-Chloro-3,6-dimethylacridine,
9-Chloro-7-methoxy-2,3-dimethylacridine,
9-Chloro-3,7-dimethoxy-2-methylacridine,
9-Chloro-2,7-dimethoxy-3-methylacridine,
9-Chloro-2,3,7-trimethoxyacridine,
9-Chloro-6-methoxy-2,3-dimethylacridine,
9-Chloro-3,6-dimethoxy-2-methylacridine,
9-Chloro-2,6-dimethoxy-3-methylacridine,
9-Chloro-2,3,6-trimethoxyacridine,
9-Chloro-3-methoxy-2,7-dimethylacridine,
9-Chloro-2-methoxy-3,7-dimethylacridine,
9-Chloro-2,3-dimethoxy-7-methylacridine,
9-Chloro-2,3,7-trimethylacridine,
9-Chloro-3-methoxy-2,6-dimethylacridine,
9-Chloro-2-methoxy-3,6-dimethylacridine,
9-Chloro-2,3-dimethoxy-6-methylacridine,
9-Chloro-2,3,7-trimethylacridine,
9-Chloro-2,3-dimethoxy-6,7-dimethylacridine,
9-Chloro-2,3,6-trimethoxy-7-methylacridine,
9-Chloro-2,3,7-trimethoxy-6-methylacridine,
9-Chloro-2,3,6,7-tetramethoxyacridine,
9-Chloro-2-methoxy-3,6,7-trimethylacridine,
9-Chloro-3-methoxy-2,6,7-trimethylacridine,
9-Chloro-2,3,6,7-tetramethylacridine.

Example 4

A mixture of 9-chloro-3-methoxyacridine, (975 mg, 4 mmol), 3-aminophenethyl alcohol (549 mg, 4 ml) and methanesulfonic acid (0.32 ml, 5 mmol) in methanol (30 ml) is stirred under reflux for 2 hours. The mixture is concentrated in vacuo, and the residue is dissolved in methanol (10 ml). The solution is diluted with ether (150 ml). The precipitates are collected by filtration, washed with ether to give 9-[3'-(β-hydroxyethyl)anilino]-3-methoxyacridine, as the methanesulfonate (1.15 g, 65%), mp 186°–188° C.

Microanalyses Calculated for $C_{22}H_{20}N_2O_2$—$CH_3SO_3H$: C, 2.71; H, 5.49; N, 6.36; S, 7.28%. Found: C, 62.79; H, 5.51; N, 6.14; S. 7.17%.

By following the same procedure but using the corresponding 9-chloroacridines and subsituted anilines, the following compounds are synthesized:
9-(2'-Hydroxymethyl)anilinoacridine,
9-(2'-Hydroxymethyl)anilino-2-methoxyacridine,
9-(3'-Hydroxymethyl)anilinoacridine,
9-(3'-Hydroxymethyl)anilino-2-methoxyacridine,
9-(3'-Hydroxymethyl)anilino-3-methoxyacridine,
9-(3'-Hydroxymethyl)anilino-2-methylacridine,
9-(3'-Hydroxymethyl)anilino-3-methylacridine,
9-(3'-Hydroxymethyl)anilino-2-methoxy-6-methylacridine,
9-(3'-Hydroxymethyl)anilino-2-methoxy-7-methylacridine,
9-(3'-Hydroxymethyl)anilino-2,6-dimethoxyacridine,
9-(3'-Hydroxymethyl)anilino-2,7-dimethoxyacridine,
9-(3'-Hydroxymethyl)anilino-3-methoxy-6-methylacridine,
9-(3'-Hydroxymethyl)anilino-6-methoxy-2-methylacridine,
9-(3'-Hydroxymethyl)anilino-3,6-dimethoxyacridine
9-(3'-Hydroxymethyl)anilino-2,6-dimethylacridine,
9-(3'-Hydroxymethyl)anilino-2,7-dimethylacridine,
9-(3'-Hydroxymethyl)anilino-3,6-dimethylacridine,
9-(3'-Hydroxymethyl)anilino-7-methoxy-2,3-dimethylacridine,
9-(3'-Hydroxymethyl)anilino-2,6-dimethoxy-7-methylacridine,
9-(3'-Hydroxymethyl)anilino-2,7-dimethoxy-3-methylacridine,
9-(3'-Hydroxymethyl)anilino-2,3,7-trimethoxyacridine,
9-(3'-Hydroxymethyl)anilino-6-methoxy-2,3-dimethylacridine,
9-(3'-Hydroxymethyl)anilino-3,6-dimethoxy-2-methylacridine, 9-(3'-Hydroxymethyl)anilino-2,6-dimethoxy-3-methylacridine,
9-(3'-Hydroxymethyl)anilino-2,3,6-trimethoxyacridine,
9-(3'-Hydroxymethyl)anilino-3-methoxy-2,7-dimethylacridine,
9-(3'-Hydroxymethyl)anilino-2-methoxy-3,7-dimethylacridine,
9-(3'-Hydroxymethyl)anilino-2,3-dimethoxy-7-methylacridine,
9-(3'-Hydroxymethyl)anilino-2,3,7-trimethylacridine,
9-(3'-Hydroxymethyl)anilino-3-methoxy-2,6-dimethylacridine,
9-(3'-Hydroxymethyl)anilino-2-methoxy-3,6-dimethylacridine,
9-(3'-Hydroxymethyl)anilino-2,3-dimethoxy-6-methylacridine,
9-(3'-Hydroxymethyl)anilino-2,3,6-trimethylacridine,
9-(3'-Hydroxymethyl)anilino-2,3-dimethoxy-6,7-dimethylacridine,
9-(3'-Hydroxymethyl)anilino-2,3,6-trimethoxy-7-methylacridine,
9-(3'-Hydroxymethyl)anilino-2,3,7-trimethoxy-6-methylacridine,
9-(3'-Hydroxymethyl)anilino-2,3,6,7-tetramethoxyacridine,
9-(3'-Hydroxymethyl)anilino-2-methoxy-3,6,7-trimethylacridine,
9-(3'-Hydroxymethyl)anilino-3-methoxy-2,6,7-trimethylacridine,
9-(3'-Hydroxymethyl)anilino-2,3,6,7-tetramethylacridine,
9-(4'-Hydroxymethyl)anilinoacridine,
9-(4'-Hydroxymethyl)anilino-2-methoxyacridine,
9-(4'-Hydroxymethyl)anilino-3-methoxyacridine,
9-(4'-Hydroxymethyl)anilino-2-methylacridine,
9-(4'-Hydroxymethyl)anilino-3-methylacridine,
9-(4'-Hydroxymethyl)anilino-2-methoxy-6-methylacridine,
9-(4'-Hydroxymethyl)anilino-2-methoxy-7-methylacridine,
9-(4'-Hydroxymethyl)anilino-2,6-dimethoxyacridine,
9-(4'-Hydroxymethyl)anilino-2,7-dimethoxyacridine,
9-(4'-Hydroxymethyl)anilino-3-methoxy-6-methylacridine,
9-(4'-Hydroxymethyl)anilino-6-methoxy-2-methylacridine,
9-(4'-Hydroxymethyl)anilino-3,6-dimethoxyacridine,
9-(4'-Hydroxymethyl)anilino-2,6-dimethylacridine,
9-(4'-Hydroxymethyl)anilino-2,7-dimethylacridine,
9-(4'-Hydroxymethyl)anilino-3,6-dimethylacridine,
9-(4'-Hydroxymethyl)anilino-7-methoxy-2,3-dimethylacridine,
9-(4'-Hydroxymethyl)anilino-2,6-dimethoxy-7-methylacridine,
9-(4'-Hydroxymethyl)anilino-2,7-dimethoxy-6-methylacridine,
9-(4'-Hydroxymethyl)anilino-2,3,7-trimethoxyacridine,
9-(4'-Hydroxymethyl)anilino-6-methoxy-2,3-dimethylacridine,
9-(4'-Hydroxymethyl)anilino-3,6-dimethoxy-2-methylacridine,
9-(4'-Hydroxymethyl)anilino-2,6-dimethoxy-3-methylacridine,
9-(4'-Hydroxymethyl)anilino-2,3,6-trimethoxyacridine,
9-(4'-Hydroxymethyl)anilino-3-methoxy-2,7-dimethylacridine,
9-(4'-Hydroxymethyl)anilino-2-methoxy-3,7-dimethylacridine,
9-(4'-Hydroxymethyl)anilino-2,3-dimethoxy-7-methylacridine,
9-(4'-Hydroxymethyl)anilino-2,3,7-trimethylacridine,
9-(4'-Hydroxymethyl)anilino-3-methoxy-2,6-dimethylacridine,
9-(4'-Hydroxymethyl)anilino-2-methoxy-3,6-dimethylacridine,
9-(4'-Hydroxymethyl)anilino-2,3-dimethoxy-6-methylacridine,
9-(4'-Hydroxymethyl)anilino-2,3,6-trimethylacridine,
9-(4'-Hydroxymethyl)anilino-2,3-dimethoxy-6,7-dimethylacridine,
9-(4'-Hydroxymethyl)anilino-2,3,6-trimethoxy-7-methylacridine,
9-(4'-Hydroxymethyl)anilino-2,3,7-trimethoxy-6-methylacridine,
9-(4'-Hydroxymethyl)anilino-2,3,6,7-tetramethoxyacridine,
9-(4'-Hydroxymethyl)anilino-2-methoxy-3,6,7-trimethylacridine,
9-(4'-Hydroxymethyl)anilino-3-methoxy-2,6,7-trimethylacridine,
9-(4'-Hydroxymethyl)anilino-2,3,6,7-tetramethylacridine,
9-[2'-($\beta$-Hydroxyethyl)anilinoacridine,
9-[2'-($\beta$-Hydroxyethyl)anilino-2-methoxyacridine,
9-[3'-($\beta$-Hydroxyethyl)anilinoacridine,
9-[3'-($\beta$-Hydroxyethyl)anilino-2-methoxyacridine,
9-[3'-($\beta$-Hydroxyethyl)anilino-2-methylacridine,
9-[3'-($\beta$-Hydroxyethyl)anilino-3-methylacridine,
9-[3'-($\beta$-Hydroxyethyl)anilino-2-methoxy-6-methylacridine,
9-[3'-($\beta$-Hydroxyethyl)anilino-2-methoxy-7-methylacridine,
9-[3'-($\beta$-Hydroxyethyl)anilino-2,6-dimethoxyacridine,
9-[3'-($\beta$-Hydroxyethyl)anilino-2,7-dimethoxyacridine,
9-[3'-($\beta$-Hydroxyethyl)anilino-3-methoxy-6-methylacridine,
9-[3'-($\beta$-Hydroxyethyl)anilino-6-methoxy-2-methylacridine,
9-[3'-($\beta$-Hydroxyethyl)anilino-3,6-dimethoxyacridine,
9-[3'-($\beta$-Hydroxyethyl)anilino-2,6-dimethylacridine,
9-[3'-($\beta$-Hydroxyethyl)anilino-2,7-dimethylacridine,
9-[3'-($\beta$-Hydroxyethyl)anilino-3,6-dimethylacridine,
9-[3'-($\beta$-Hydroxyethyl)anilino-7-methoxy-2,3-dimethylacridine,
9-[3'-($\beta$-Hydroxyethyl)anilino-3,7-dimethoxy-2-methylacridine,
9-[3'-($\beta$-Hydroxyethyl)anilino-2,7-dimethoxy-3-methylacridine,
9-[3'-($\beta$-Hydroxyethyl)anilino-2,3,7-trimethoxyacridine,
9-[3'-($\beta$-Hydroxyethyl)anilino-6-methoxy-2,3-dimethylacridine,
9-[3'-($\beta$-Hydroxyethyl)anilino-3,6-dimethoxy-2-methylacridine,
9-[3'-($\beta$-Hydroxyethyl)anilino-2,6-dimethoxy-3-methylacridine,
9-[3'-($\beta$-Hydroxyethyl)anilino-2,3,6-trimethoxyacridine,
9-[3'-($\beta$-Hydroxyethyl)anilino-3-methoxy-2,7-dimethylacridine,
9-[3'-($\beta$-Hydroxyethyl)anilino-2-methoxy-3,7-dimethylacridine,
9-[3'-($\beta$-Hydroxyethyl)anilino-2,3-dimethoxy-7-methylacridine,
9-[3'-($\beta$-Hydroxyethyl)anilino-2,3,7-trimethylacridine, 9-[3'-(β-Hydroxyethyl)anilino-3-methoxy-2,6-dimethylacridine,
9-[3'-(β-Hydroxyethyl)anilino-2-methoxy-3,6-dimethylacridine,
9-[3'-(β-Hydroxyethyl)anilino-2,3-dimethoxy-6-methylacridine,
9-[3'-(β-Hydroxyethyl)anilino-2,3,6-trimethylacridine,
9-[3'-(β-Hydroxyethyl)anilino-2,3-dimethoxy-6,7-dimethylacridine,
9-[3'-(β-Hydroxyethyl)anilino-2,3,6-trimethoxy-7-methylacridine,
9-[3'-(β-Hydroxyethyl)anilino-2,3,7-trimethoxy-6-methylacridine,
9-[3'-(β-Hydroxyethyl)anilino-2,3,6,7-tetramethoxyacridine,
9-[3'-(β-Hydroxyethyl)anilino-2-methoxy-3,6,7-trimethylacridine,
9-[3'-(β-Hydroxyethyl)anilino-3-methoxy-2,6,7-trimethylacridine,
9-[3'-(β-Hydroxyethyl)anilino-2,3,6,7-tetramethylacridine,
9-[4'-(β-Hydroxyethyl)anilinoacridine,
9-[4'-(β-Hydroxyethyl)anilino-2-methoxyacridine,
9-[4'-(β-Hydroxyethyl)anilino-3-methoxyacridine,
9-[4'-(β-Hydroxyethyl)anilino-2-methylacridine,
9-[4'-(β-Hydroxyethyl)anilino-3-methylacridine,
9-[4'-(β-Hydroxyethyl)anilino-2-methoxy-6-methylacridine,
9-[4'-(β-Hydroxyethyl)anilino-2-methoxy-7-methylacridine,
9-[4'-(β-Hydroxyethyl)anilino-2,6-dimethoxyacridine,
9-[4'-(β-Hydroxyethyl)anilino-2,7-dimethoxyacridine,
9-[4'-(β-Hydroxyethyl)anilino-3-methoxy-6-methylacridine,
9-[4'-(β-Hydroxyethyl)anilino-6-methoxy-2-methylacridine,
9-[4'-(β-Hydroxyethyl)anilino-3,6-dimethoxyacridine,
9-[4'-(β-Hydroxyethyl)anilino-2,6-dimethylacridine,
9-[4'-(β-Hydroxyethyl)anilino-2,7-dimethylacridine,
9-[4'-(β-Hydroxyethyl)anilino-3,6-dimethylacridine,
9-[4'-(β-Hydroxyethyl)anilino-7-methoxy-2,3-dimethylacridine,
9-[4'-(β-Hydroxyethyl)anilino-3,7-dimethoxy-2-methylacridine,
9-[4'-(β-Hydroxyethyl)anilino-2,7-dimethoxy-3-methylacridine,
9-[4'-(β-Hydroxyethyl)anilino-2,3,7-trimethoxyacridine,
9-[4'-(β-Hydroxyethyl)anilino-6-methoxy-2,3-dimethylacridine,
9-[4'-(β-Hydroxyethyl)anilino-3,6-dimethoxy-2-methylacridine,
9-[4'-(β-Hydroxyethyl)anilino-2,6-dimethoxy-3-methylacridine,
9-[4'-(β-Hydroxyethyl)anilino-2,3,6-trimethoxyacridine,
9-[4'-(β-Hydroxyethyl)anilino-3-methoxy-2,7-dimethylacridine,
9-[4'-(β-Hydroxyethyl)anilino-2-methoxy-3,7-dimethylacridine,
9-[4'-(β-Hydroxyethyl)anilino-2,3-dimethoxy-7-methylacridine,
9-[4'-(β-Hydroxyethyl)anilino-2,3,7-trimethylacridine,
9-[4'-(β-Hydroxyethyl)anilino-3-methoxy-2,6-dimethylacridine,
9-[4'-(β-Hydroxyethyl)anilino-2-methoxy-3,6-dimethylacridine,
9-[4'-(β-Hydroxyethyl)anilino-2,3-dimethoxy-6-methylacridine,
9-[4'-(β-Hydroxyethyl)anilino-2,3,6-trimethylacridine,
9-[4'-(β-Hydroxyethyl)anilino-2,3-dimethoxy-6,7-dimethylacridine,
9-[4'-(β-Hydroxyethyl)anilino-2,3,6-trimethoxy-7-methylacridine,
9-[4'-(β-Hydroxyethyl)anilino-2,3,7-trimethoxy-6-methylacridine,
9-[4'-(β-Hydroxyethyl)anilino-2,3,6,7-tetramethoxyacridine,
9-[4'-(β-Hydroxyethyl)anilino-2-methoxy-3,6,7-trimethylacridine,
9-[4'-(β-Hydroxyethyl)anilino-3-methoxy-2,6,7-trimethylacridine,
9-[4'-(β-Hydroxyethyl)anilino-2,3,6,7-tetramethoxyacridine.

Example 5

A mixture of 9-(3'-hydroxymethylanilino)-2,7-dimethoxyacridine, (300 mg, 0.66 mmol), isopropyl isocyanate (1 ml) and triethylamine (2 ml) in methylene chloride (20 ml) is stirred at room temperature for 90 minutes, and then concentrated in vacuo. The residue is chromatographed on a silica gel column using commerical chloroform as the eluent to give the 9-[3'-(isopropylaminocarbonyloxymethyl)-anilino]-2,7-dimethoxyacridine, (246 mg, 84%) as a yellow solid, mp 148°–149° C.

Microanalyses. Calculated for $C_{26}H_{27}N_3O_4$: C, 70.10; H, 6.11; N, 9.43%. Found: C, 69.88; H, 6.22; N, 9.68%.

By following the same procedure but using the corresponding 9-chloroacridines and substituted anilines, the following compounds are prepared:

9-[2'-(Methylaminocarbonyloxymethyl)anilino]acridine,
9-[2'-(Isopropylaminocarbonyloxymethyl)anilino]acridine,
9-[3'-(Methylaminocarbonyloxymethyl)anilino]acridine,
9-[3'-(Methylaminocarbonyloxymethyl)anilino]-2-methoxyacridine,
9-[3'-(Methylaminocarbonyloxymethyl)anilino]-3-methoxyacridine,
9-[3'-(Methylaminocarbonyloxymethyl)anilino]-2-methylacridine,
9-[3'-(Methylaminocarbonyloxymethyl)anilino]-3-methylacridine,
9-[3'-(Methylaminocarbonyloxymethyl)anilino]-2-methoxy-6-methylacridine,
9-[3'-(Methylaminocarbonyloxymethyl)anilino]-2-methoxy-7-methylacridine,
9-[3'-(Methylaminocarbonyloxymethyl)anilino]-2,6-dimethoxyacridine,
9-[3'-(Methylaminocarbonyloxymethyl)anilino]-2,7-dimethoxyacridine,
9-[3'-(Methylaminocarbonyloxymethyl)anilino]-3-methoxy-6-methylacridine,
9-[3'-(Methylaminocarbonyloxymethyl)anilino]-6-methoxy-2-methylacridine,
9-[3'-(Methylaminocarbonyloxymethyl)anilino]-3,6-dimethoxyacridine,
9-[3'-(Methylaminocarbonyloxymethyl)anilino]-2,6-dimethylacridine,
9-[3'-(Methylaminocarbonyloxymethyl)anilino]-3,6-dimethylacridine,
9-[3'-(Methylaminocarbonyloxymethyl)anilino]-7-methoxy-2,3-dimethylacridine, 9-[3'-(Methylaminocarbonyloxymethyl)anilino]-2,6-dimethoxy-7-methylacridine,
9-[3'-(Methylaminocarbonyloxymethyl)anilino]-2,7-dimethoxy-3-methylacridine,
9-[3'-(Methylaminocarbonyloxymethyl)anilino]-2,3,7-trimethoxyacridine,
9-[3'-(Methylaminocarbonyloxymethyl)anilino]-6-methoxy-2,3-dimethylacridine,
9-[3'-(Methylaminocarbonyloxymethyl)anilino]-3,6-dimethoxy-2-methylacridine,
9-[3'-(Methylaminocarbonyloxymethyl)anilino]-2,3,6-trimethoxyacridine,
9-[3'-(Methylaminocarbonyloxymethyl)anilino]-3-methoxy-2,7-dimethylacridine,
9-[3'-(Methylaminocarbonyloxymethyl)anilino]-2-methoxy-3,7-dimethylacridine,
9-[3'-(Methylaminocarbonyloxymethyl)anilino]-2,3-dimethoxy-7-methylacridine,
9-[3'-(Methylaminocarbonyloxymethyl)anilino]-2,3,7-trimethylacridine,
9-[3'-(Methylaminocarbonyloxymethyl)anilino]-3-methoxy-2,6-dimethylacridine,
9-[3'-(Methylaminocarbonyloxymethyl)anilino]-2-methoxy-3,6-dimethylacridine,
9-[3'-(Methylaminocarbonyloxymethyl)anilino]-2,3-dimethoxy-6-methylacridine,
9-[3'-(Methylaminocarbonyloxymethyl)anilino]-2,3,6-trimethylacridine,
9-[3'-(Methylaminocarbonyloxymethyl)anilino]-2,3-dimethoxy-6,7-dimethylacridine,
9-[3'-(Methylaminocarbonyloxymethyl)anilino]-2,3,6-trimethoxy-7-methylacridine,
9-[3'-(Methylaminocarbonyloxymethyl)anilino]-2,3,7-trimethoxy-6-methylacridine,
9-[3'-(Methylaminocarbonyloxymethyl)anilino]-2,3,6,7-tetramethoxyacridine,
9-[3'-(Methylaminocarbonyloxymethyl)anilino]-2-methoxy-3,6,7-trimethylacridine,
9-[3'-(Methylaminocarbonyloxymethyl)anilino]-3-methoxy-2,6,7-trimethylacridine,
9-[3'-(Methylaminocarbonyloxymethyl)anilino]-2,3,6,7-tetramethylacridine,
9-[3'-(Isopropylaminocarbonyloxymethyl)anilino]acridine,
9-[3'-(Isopropylaminocarbonyloxymethyl)anilino]-2-methoxyacridine,
9-[3'-(Isopropylaminocarbonyloxymethyl)anilino]-3-methoxyacridine,
9-[3'-(Isopropylaminocarbonyloxymethyl)anilino]-2-methylacridine,
9-[3'-(Isopropylaminocarbonyloxymethyl)anilino]-3-methylacridine,
9-[3'-(Isopropylaminocarbonyloxymethyl)anilino]-2-methoxy-6-methylacridine,
9-[3'-(Isopropylaminocarbonyloxymethyl)anilino]-2-methoxy-7-methylacridine,
9-[3'-(Isopropylaminocarbonyloxymethyl)anilino]-2,6-dimethoxyacridine,
9-[3'-(Isopropylaminocarbonyloxymethyl)anilino]-3-methoxy-6-methylacridine,
9-[3'-(Isopropylaminocarbonyloxymethyl)anilino]-6-methoxy-2-methylacridine,
9-[3'-(Isopropylaminocarbonyloxymethyl)anilino]-3,6-dimethoxyacridine,
9-[3'-(Isopropylaminocarbonyloxymethyl)anilino]-2,6-dimethylacridine,
9-[3'-(Isopropylaminocarbonyloxymethyl)anilino]-2,7-dimethylacridine,
9-[3'-(Isopropylaminocarbonyloxymethyl)anilino]-3,6-dimethylacridine,
9-[1,-(Isopropylaminocarbonyloxymethyl)anilino]-7-methoxy-2,3-dimethylacridine,
9-[3'-(Isopropylaminocarbonyloxymethyl)anilino]-2,6-dimethoxy-7-dimethylacridine,
9-[3'-(Isopropylaminocarbonyloxymethyl)anilino]-2,7-dimethoxy-3-dimethylacridine,
9-[3'-(Isopropylaminocarbonyloxymethyl)anilino]-2,3,7-trimethoxyacridine,
9-[3'-(Isopropylaminocarbonyloxymethyl)anilino]-6-methoxy-2,3-dimethylacridine,
9-[3'-(Isopropylaminocarbonyloxymethyl)anilino]-3,6-dimethoxy-2-methylacridine,
9-[3'-(Isopropylaminocarbonyloxymethyl)anilino]-2,6-dimethoxy-3-methylacridine,
9-[3'-(Isopropylaminocarbonyloxymethyl)anilino]-2,3-trimethoxyacridine,
9-[3'-(Isopropylaminocarbonyloxymethyl)anilino]-3-methoxy-2,7-dimethylacridine,
9-[3'-(Isopropylaminocarbonyloxymethyl)anilino]-2-methoxy-3,7-dimethylacridine,
9-[3'-(Isopropylaminocarbonyloxymethyl)anilino]-2,3-methoxy-7-methylacridine,
9-[3'-(Isopropylaminocarbonyloxymethyl)anilino]-2,3,7-trimethylacridine,
9-[3'-(Isopropylaminocarbonyloxymethyl)anilino]-3-methoxy-2,6-dimethylacridine,
9-[3'-(Isopropylaminocarbonyloxymethyl)anilino]-2-methoxy-3,6-dimethylacridine,
9-[3'-(Isopropylaminocarbonyloxymethyl)anilino]-2,3-dimethoxy-6-methylacridine,
9-[3'-(Isopropylaminocarbonyloxymethyl)anilino]-2,3,6-trimethylacridine,
9-[3'-(Isopropylaminocarbonyloxymethyl)anilino]-2,3-dimethoxy-6,7-dimethylacridine,
9-[3'-(Isopropylaminocarbonyloxymethyl)anilino]-2,3,6-trimethoxy-7-methylacridine,
9-[3'-(Isopropylaminocarbonyloxymethyl)anilino]-2,3,7-trimethoxy-6-methylacridine,
9-[3'-(Isopropylaminocarbonyloxymethyl)anilino]-2,3,6,7-tetramethoxyacridine,
9-[3'-(Isopropylaminocarbonyloxymethyl)anilino]-2-methoxy-3,6,7-trimethylacridine,
9-[3'-(Isopropylaminocarbonyloxymethyl)anilino]-3-methoxy-2,6,7-trimethylacridine,
9-[3'-(Isopropylaminocarbonyloxymethyl)anilino]-2,3,6,7-tetramethylacridine,
9-[4'-(Methylaminocarbonyloxymethyl)anilino]acridine,
9-[4'-(Methylaminocarbonyloxymethyl)anilino]-2-methoxyacridine,
9-[4'-(Methylaminocarbonyloxymethyl)anilino]-3-methoxyacridine,
9-[4'-(Methylaminocarbonyloxymethyl)anilino]-2-methylacridine,
9-[4'-(Methylaminocarbonyloxymethyl)anilino]-3-methylacridine,
9-[4'-(Methylaminocarbonyloxymethyl)anilino]-2-methoxy-6-methylacridine,
9-[4'-(Methylaminocarbonyloxymethyl)anilino]-2-methoxy-7-methylacridine,
9-[4'-(Methylaminocarbonyloxymethyl)anilino]-2,6-dimethoxyacridine,
9-[4'-(Methylaminocarbonyloxymethyl)anilino]-2,7-dimethoxyacridine,
9-[4'-(Methylaminocarbonyloxymethyl)anilino]-3-methoxy-6-methylacridine, 9-[4'-(Methylaminocarbonyloxymethyl)anilino]-6-methoxy-2-methylacridine,
9-[4'-(Methylaminocarbonyloxymethyl)anilino]-3,6-dimethoxyacridine,
9-[4'-(Methylaminocarbonyloxymethyl)anilino]-2,6-dimethylacridine,
9-[4'-(Methylaminocarbonyloxymethyl)anilino]-2,7-dimethylacridine,
9-[4'-(Methylaminocarbonyloxymethyl)anilino]-3,6-dimethylacridine,
9-[4'-(Methylaminocarbonyloxymethyl)anilino]-2,6-dimethoxy-7-methylacridine,
9-[4'-(Methylaminocarbonyloxymethyl)anilino]-2,7-dimethoxy-7-methylacridine,
9-[4'-(Methylaminocarbonyloxymethyl)anilino]-2,3,7-trimethoxyacridine,
9-[4'-(Methylaminocarbonyloxymethyl)anilino]-6-methoxy-2,3-dimethylacridine,
9-[4'-(Methylaminocarbonyloxymethyl)anilino]-3,6-dimethoxy-2-methylacridine,
9-[4'-(Methylaminocarbonyloxymethyl)anilino]-2,6-dimethoxy-3-methylacridine,
9-[4'-(Methylaminocarbonyloxymethyl)anilino]-2,3,6-trimethoxyacridine,
9-[4'-(Methylaminocarbonyloxymethyl)anilino]-3-methoxy-2,7-dimethylacridine,
9-[4'-(Methylaminocarbonyloxymethyl)anilino]-2-methoxy-3,7-dimethylacridine,
9-[4'-(Methylaminocarbonyloxymethyl)anilino]-2,3-dimethoxy-7-methylacridine,
9-[4'-(Methylaminocarbonyloxymethyl)anilino]-2,3,7-trimethylacridine,
9-[4'-(Methylaminocarbonyloxymethyl)anilino]-3-methoxy-2,6-dimethylacridine,
9-[4'-(Methylaminocarbonyloxymethyl)anilino]-2-methoxy-3,6-dimethylacridine,
9-[4'-(Methylaminocarbonyloxymethyl)anilino]-2,3-dimethoxy-6-methylacridine,
9-[4'-(Methylaminocarbonyloxymethyl)anilino]-2,3,6-trimethylacridine,
9-[4'-(Methylaminocarbonyloxymethyl)anilino]-2,3-dimethoxy-6,7-dimethylacridine,
9-[4'-(Methylaminocarbonyloxymethyl)anilino]-2,3,6-trimethoxy-7-methylacridine,
9-[4'-(Methylaminocarbonyloxymethyl)anilino]-2,3,7-trimethoxy-6-methylacridine,
9-[4'-(Methylaminocarbonyloxymethyl)anilino]-2,3,6,7-tetramethoxyacridine,
9-[4'-(Methylaminocarbonyloxymethyl)anilino]-2-methoxy-3,6,7-trimethylacridine,
9-[4'-(Methylaminocarbonyloxymethyl)anilino]-3-methoxy-2,6,7-trimethylacridine,
9-[4'-(Methylaminocarbonyloxymethyl)anilino]-2,3,6,7-tetramethylacridine,
9-[4'-(Isopropylaminocarbonyloxymethyl)anilino]acridine,
9-[4'-(Isopropylaminocarbonyloxymethyl)anilino]-2-methoxyacridine,
9-[4'-(Isopropylaminocarbonyloxymethyl)anilino]-3-methoxyacridine,
9-[4'-(Isopropylaminocarbonyloxymethyl)anilino]-2-methylacridine,
9-[4'-(Isopropylaminocarbonyloxymethyl)anilino]-3-methylacridine,
9-[4'-(Isopropylaminocarbonyloxymethyl)anilino]-2-methoxy-6-methylacridine,
9-[4'-(Isopropylaminocarbonyloxymethyl)anilino]-2-methoxy-7-methylacridine,
9-[4'-(Isopropylaminocarbonyloxymethyl)anilino]-2,6-dimethoxyacridine,
9-[4'-(Isopropylaminocarbonyloxymethyl)anilino]-2,7-dimethoxyacridine,
9-[4'-(Isopropylaminocarbonyloxymethyl)anilino]-3-methoxy-6-methylacridine,
9-[4'-(Isopropylaminocarbonyloxymethyl)anilino]-6-methoxy-2-methylacridine,
9-[4'-(Isopropylaminocarbonyloxymethyl)anilino]-3,6-dimethoxyacridine,
9-[4'-(Isopropylaminocarbonyloxymethyl)anilino]-2,6-dimethylacridine,
9-[4'-(Isopropylaminocarbonyloxymethyl)anilino]-2,7-dimethylacridine,
9-[4'-(Isopropylaminocarbonyloxymethyl)anilino]-3,6-dimethylacridine,
9-[4'-(Isopropylaminocarbonyloxymethyl)anilino]-7-methoxy-2,3-dimethylacridine,
9-[4'-(Isopropylaminocarbonyloxymethyl)anilino]-2,6-dimethoxy-7-dimethylacridine,
9-[4'-(Isopropylaminocarbonyloxymethyl)anilino]-2,7-dimethoxy-3-methylacridine,
9-[4'-(Isopropylaminocarbonyloxymethyl)anilino]-2,3,7-trimethoxyacridine,
9-[4'-(Isopropylaminocarbonyloxymethyl)anilino]-6-methoxy-2,3-dimethylacridine,
9-[4'-(Isopropylaminocarbonyloxymethyl)anilino]-3,6-dimethoxy-2-methylacridine,
9-[4'-(Isopropylaminocarbonyloxymethyl)anilino]-2,6-dimethoxy-3-methylacridine,
9-[4'-(Isopropylaminocarbonyloxymethyl)anilino]-2,3,6-trimethoxyacridine,
9-[4'-(Isopropylaminocarbonyloxymethyl)anilino]-3-methoxy-2,7-dimethylacridine,
9-[4'-(Isopropylaminocarbonyloxymethyl)anilino]-2-methoxy-3,7-dimethylacridine,
9-[4'-(Isopropylaminocarbonyloxymethyl)anilino]-2,3-methoxy-7-methylacridine,
9-[4'-(Isopropylaminocarbonyloxymethyl)anilino]-2,3,7-trimethylacridine,
9-[4'-(Isopropylaminocarbonyloxymethyl)anilino]-3-methoxy-2,6-dimethylacridine,
9-[4'-(Isopropylaminocarbonyloxymethyl)anilino]-2-methoxy-3,6-dimethylacridine,
9-[4'-(Isopropylaminocarbonyloxymethyl)anilino]-2,3-dimethoxy-6-methylacridine,
9-[4'-(Isopropylaminocarbonyloxymethyl)anilino]-2,3,6-trimethylacridine,
9-[4'-(Isopropylaminocarbonyloxymethyl)anilino]-2,3-dimethoxy-6,7-dimethylacridine,
9-[4'-(Isopropylaminocarbonyloxymethyl)anilino]-2,3,6-trimethoxy-7-methylacridine,
9-[4'-(Isopropylaminocarbonyloxymethyl)anilino]-2,3,7-trimethoxy-6-methylacridine,
9-[4'-(Isopropylaminocarbonyloxymethyl)anilino]-2,3,6,7-tetramethoxyacridine,
9-[4'-(Isopropylaminocarbonyloxymethyl)anilino]-2-methoxy-3,6,7-trimethylacridine,
9-[4'-(Isopropylaminocarbonyloxymethyl)anilino]-3-methoxy-2,6,7-trimethylacridine,
9-[4'-(Isopropylaminocarbonyloxymethyl)anilino]-2,3,6,7-tetramethylacridine,
9-[2'-(β-Methylaminocarbonyloxyethyl)anilino]acridine,
9-[2'-(β-Isopropylaminocarbonyloxyethyl)anilino]acridine,
9-[3'-(β-Methylaminocarbonyloxyethyl)anilino]acridine, 9-[3'-(β-Methylaminocarbonyloxyethyl)anilino]-2-methoxyacridine,
9-[3'-(β-Methylaminocarbonyloxyethyl)anilino]-3-methoxyacridine,
9-[3'-(β-Methylaminocarbonyloxyethyl)anilino]-2-methylacridine,
9-[3'-(β-Methylaminocarbonyloxyethyl)anilino]-3-methylacridine,
9-[3'-(β-Methylaminocarbonyloxyethyl)anilino]-2-methoxy-6-methylacridine,
9-[3'-(β-Methylaminocarbonyloxyethyl)anilino]-2-methoxy-7-methylacridine,
9-[3'-(β-Methylaminocarbonyloxyethyl)anilino]-2,6-dimethoxyacridine,
9-[3'-(β-Methylaminocarbonyloxyethyl)anilino]-2,7-dimethoxyacridine,
9-[3'-(β-Methylaminocarbonyloxyethyl)anilino]-3-methoxy-6-methylacridine,
9-[3'-(β-Methylaminocarbonyloxyethyl)anilino]-6-methoxy-2-methylacridine,
9-[3'-(β-Methylaminocarbonyloxyethyl)anilino]-3,6-dimethoxyacridine,
9-[3'-(β-Methylaminocarbonyloxyethyl)anilino]-2,6-dimethylacridine,
9-[3'-(β-Methylaminocarbonyloxyethyl)anilino]-3,6-dimethylacridine,
9-[3'-(β-Methylaminocarbonyloxyethyl)anilino]-7-methoxy-2,3-dimethylacridine,
9-[3'-(β-Methylaminocarbonyloxyethyl)anilino]-2,6-dimethoxy-7-methylacridine,
9-[3'-(β-Methylaminocarbonyloxyethyl)anilino]-2,7-dimethoxy-3-methylacridine,
9-[3'-(β-Methylaminocarbonyloxyethyl)anilino]-2,3,7-trimethoxyacridine,
9-[3'-(β-Methylaminocarbonyloxyethyl)anilino]-6-methoxy-2,3-dimethylacridine,
9-[3'-(β-Methylaminocarbonyloxyethyl)anilino]-3,6-dimethoxy-2-methylacridine,
9-[3'-(β-Methylaminocarbonyloxyethyl)anilino]-2,3,6-trimethoxyacridine,
9-[3'-(β-Methylaminocarbonyloxyethyl)anilino]-3-methoxy-2,7-dimethylacridine,
9-[3'-(β-Methylaminocarbonyloxyethyl)anilino]-2-methoxy-3,7-dimethylacridine,
9-[3'-(β-Methylaminocarbonyloxyethyl)anilino]-2,3-dimethoxy-7-methylacridine,
9-[3'-(β-Methylaminocarbonyloxyethyl)anilino]-2,3,7-trimethylacridine,
9-[3'-(β-Methylaminocarbonyloxyethyl)anilino]-3-methoxy-2,6-dimethylacridine,
9-[3'-(β-Methylaminocarbonyloxyethyl)anilino]-2-methoxy-3,6-dimethylacridine,
9-[3'-(β-Methylaminocarbonyloxyethyl)anilino]-2,3-dimethoxy-6-methylacridine,
9-[3'-(β-Methylaminocarbonyloxyethyl)anilino]-2,3,6-trimethylacridine,
9-[3'-(β-Methylaminocarbonyloxyethyl)anilino]-2,3-dimethoxy-6,7-dimethylacridine,
9-[3'-(β-Methylaminocarbonyloxyethyl)anilino]-2,3,6-trimethoxy-7-methylacridine,
9-[3'-(β-Methylaminocarbonyloxyethyl)anilino]-2,3,7-trimethoxy-6-methylacridine,
9-[3'-(β-Methylaminocarbonyloxyethyl)anilino]-2,3,6,7-tetramethoxyacridine,
9-[3'-(β-Methylaminocarbonyloxyethyl)anilino]-2-methoxy-3,6,7-trimethylacridine,
9-[3'-(β-Methylaminocarbonyloxyethyl)anilino]-3-methoxy-2,6,7-trimethylacridine,
9-[3'-(β-Methylaminocarbonyloxyethyl)anilino]-2,3,6,7-tetramethylacridine,
9-[3'-(β-Isopropylaminocarbonyloxyethyl)anilino]acridine,
9-[3'-(β-Isopropylamino#pqbonyloxyethyl)anilino]-2-methoxyacridine,
9-[3'-(β-Isopropylaminocarbonyloxyethyl)anilino]-3-methoxyacridine,
9-[3'-(β-Isopropylaminocarbonyloxyethyl)anilino]-2-methylacridine,
9-[3'-(β-Isopropylaminocarbonyloxyethyl)anilino]-3-methylacridine,
9-[3'-(β-Isopropylaminocarbonyloxyethyl)anilino]-2-methoxy-6-methylacridine,
9-[3'-(β-Isopropylaminocarbonyloxyethyl)anilino]-2-methoxy-7-methylacridine,
9-[3'-(β-Isopropylaminocarbonyloxyethyl)anilino]-2,6-dimethoxyacridine,
9-[3'-(β-Isopropylaminocarbonyloxyethyl)anilino]-2,7-dimethoxyacridine,
9-[3'-(β-Isopropylaminocarbonyloxyethyl)anilino]-3-methoxy-6-methylacridine,
9-[3'-(β-Isopropylaminocarbonyloxyethyl)anilino]-6-methoxy-2-methylacridine,
9-[3'-(β-Isopropylaminocarbonyloxyethyl)anilino]-3,6-dimethoxyacridine,
9-[3'-(β-Isopropylaminocarbonyloxyethyl)anilino]-2,6-dimethylacridine,
9-[3'-(β-Isopropylaminocarbonyloxyethyl)anilino]-2,7-dimethylacridine,
9-[3'-(β-Isopropylaminocarbonyloxyethyl)anilino]-3,6-dimethylacridine,
9-[3'-(β-Isopropylaminocarbonyloxyethyl)anilino]-7-methoxy-2,3-dimethylacridine,
9-[3'-(β-Isopropylaminocarbonyloxyethyl)anilino]-2,6-dimethoxy-7-dimethylacridine,
9-[3'-(β-Isopropylaminocarbonyloxyethyl)anilino]-2,7-dimethoxy-3-methylacridine,
9-[3'-(β-Isopropylaminocarbonyloxyethyl)anilino]-2,3,6-trimethoxyacridine,
9-[3'-(β-Isopropylaminocarbonyloxyethyl)anilino]-6-methoxy-2,3-dimethylacridine,
9-[3'-(β-Isopropylaminocarbonyloxyethyl)anilino]-3,6-dimethoxy-2-methylacridine,
9-[3'-(β-Isopropylaminocarbonyloxyethyl)anilino]-2,6-dimethoxy-3-methylacridine,
9-[3'-(β-Isopropylaminocarbonyloxyethyl)anilino]-2,3,7-trimethoxyacridine,
9-[3'-(β-Isopropylaminocarbonyloxyethyl)anilino]-3-methoxy-2,7-dimethylacridine,
9-[3'-(β-Isopropylaminocarbonyloxyethyl)anilino]-2-methoxy-3,7-dimethylacridine,
9-[3'-(β-Isopropylaminocarbonyloxyethyl)anilino]-2,3-dimethoxy-7-methylacridine,
9-[3'-(β-Isopropylaminocarbonyloxyethyl)anilino]-2,3,7-trimethylacridine,
9-[3'-(β-Isopropylaminocarbonyloxyethyl)anilino]-3-methoxy-2,6-dimethylacridine,
9-[3'-(β-Isopropylaminocarbonyloxyethyl)anilino]-2-methoxy-3,6-dimethylacridine,
9-[3'-(β-Isopropylaminocarbonyloxyethyl)anilino]-2,3-dimethoxy-6-methylacridine,
9-[3'-(β-Isopropylaminocarbonyloxyethyl)anilino]-2,3,6-trimethylacridine,
9-[3'-(β-Isopropylaminocarbonyloxyethyl)anilino]-2,3-dimethoxy-6,7-dimethylacridine,
9-[3'-(β-Isopropylaminocarbonyloxyethyl)anilino]-2,3,6-trimethoxy-7-methylacridine, 9-[3'-(β-Isopropylaminocarbonyloxyethyl)anilino]-2,3,7-trimethoxy-6-methylacridine,
9-[3'-(β-Isopropylaminocarbonyloxyethyl)anilino]-2,3,6,7-tetramethoxyacridine,
9-[3'-(β-Isopropylaminocarbonyloxyethyl)anilino]-2-methoxy-3,6,7-trimethylacridine,
9-[3'-(β-Isopropylaminocarbonyloxyethyl)anilino]-3-methoxy-2,6,7-trimethylacridine,
9-[3'-(β-Isopropylaminocarbonyloxyethyl)anilino]-2,3,6,7-tetramethylacridine,
9-[4'-(β-Methylaminocarbonyloxyethyl)anilino]acridine,
9-[4'-(β-Methylaminocarbonyloxyethyl)anilino]-2-methoxyacridine,
9-[4'-(β-Methylaminocarbonyloxyethyl)anilino]-3-methoxyacridine,
9-[4'-(β-Methylaminocarbonyloxyethyl)anilino]-2-methylacridine,
9-[4'-(β-Methylaminocarbonyloxyethyl)anilino]-3-methylacridine,
9-[4'-(β-Methylaminocarbonyloxyethyl)anilino]-2-methoxy-6-methylacridine,
9-[4'-(β-Methylaminocarbonyloxyethyl)anilino]-2-methoxy-7-methylacridine,
9-[4'-(β-Methylaminocarbonyloxyethyl)anilino]-2,6-dimethoxyacridine,
9-[4'-(β-Methylaminocarbonyloxyethyl)anilino]-2,7-dimethoxyacridine,
9-[4'-(β-Methylaminocarbonyloxyethyl)anilino]-3-methoxy-6-methylacridine,
9-[4'-(β-Methylaminocarbonyloxyethyl)anilino]-6-methoxy-2-methylacridine,
9-[4'-(β-Methylaminocarbonyloxyethyl)anilino]-3,6-dimethoxyacridine,
9-[4'-(β-Methylaminocarbonyloxyethyl)anilino]-2,6-dimethylacridine,
9-[4'-(β-Methylaminocarbonyloxyethyl)anilino]-2,7-dimethylacridine,
9-[4'-(β-Methylaminocarbonyloxyethyl)anilino]-3,6-dimethylacridine,
9-[4'-(β-Methylaminocarbonyloxyethyl)anilino]-2,6-dimethoxy-7-methylacridine,
9-[4'-(β-Methylaminocarbonyloxyethyl)anilino]-2,7-dimethoxy-3-methylacridine,
9-[4'-(β-Methylaminocarbonyloxyethyl)anilino]-2,3,7-trimethoxyacridine,
9-[4'-(β-Methylaminocarbonyloxyethyl)anilino]-6-methoxy-2,3-dimethylacridine,
9-[4'-(β-Methylaminocarbonyloxyethyl)anilino]-3,6-dimethoxy-2-methylacridine,
9-[4'-(β-Methylaminocarbonyloxyethyl)anilino]-2,6-dimethoxy-3-methylacridine,
9-[4'-(β-Methylaminocarbonyloxyethyl)anilino]-2,3,6-trimethoxyacridine,
9-[4'-(β-Methylaminocarbonyloxyethyl)anilino]-3-methoxy-2,7-dimethylacridine,
9-[4'-(β-Methylaminocarbonyloxyethyl)anilino]-2-methoxy-3,7-dimethylacridine,
9-[4'-(β-Methylaminocarbonyloxyethyl)anilino]-2,3-dimethoxy-7-methylacridine,
9-[4'-(β-Methylaminocarbonyloxyethyl)anilino]-2,3,7-trimethylacridine,
9-[4'-(β-Methylaminocarbonyloxyethyl)anilino]-3-methoxy-2,6-dimethylacridine,
9-[4'-(β-Methylaminocarbonyloxyethyl)anilino]-2-methoxy-3,6-dimethylacridine,
9-[4'-(β-Methylaminocarbonyloxyethyl)anilino]-2,3-dimethoxy-6-methylacridine,
9-[4'-(β-Methylaminocarbonyloxyethyl)anilino]-2,3,6-trimethylacridine,
9-[4'-(β-Methylaminocarbonyloxyethyl)anilino]-2,3-dimethoxy-6,7-dimethylacridine,
9-[4'-(β-Methylaminocarbonyloxyethyl)anilino]-2,3,6-trimethoxy-7-methylacridine,
9-[4'-(β-Methylaminocarbonyloxyethyl)anilino]-2,3,7-trimethoxy-6-methylacridine,
9-[4'-(β-Methylaminocarbonyloxyethyl)anilino]-2,3,6,7-tetramethoxyacridine,
9-[4'-(β-Methylaminocarbonyloxyethyl)anilino]-2-methoxy-3,6,7-trimethylacridine,
9-[4'-(β-Methylaminocarbonyloxyethyl)anilino]-3-methoxy-2,6,7-trimethylacridine,
9-[4'-(β-Methylaminocarbonyloxyethyl)anilino]-2,3,6,7-tetramethylacridine,
9-[4'-(β-Isopropylaminocarbonyloxyethyl)anilino]acridine,
9-[4'-(β-Isopropylaminocarbonyloxyethyl)anilino]-2-methoxyacridine,
9-[4'-(β-Isopropylaminocarbonyloxyethyl)anilino]-3-methoxyacridine,
9-[4'-(β-Isopropylaminocarbonyloxyethyl)anilino]-2-methylacridine,
9-[4'-(β-Isopropylaminocarbonyloxyethyl)anilino]-3-methylacridine,
9-[4'-(β-Isopropylaminocarbonyloxyethyl)anilino]-2-methoxy-6-methylacridine,
9-[4'-(β-Isopropylaminocarbonyloxyethyl)anilino]-2-methoxy-7-methylacridine,
9-[4'-(β-Isopropylaminocarbonyloxyethyl)anilino]-2,6-dimethoxyacridine,
9-[4'-(β-Isopropylaminocarbonyloxyethyl)anilino]-2,7-dimethoxyacridine,
9-[4'-(β-Isopropylaminocarbonyloxyethyl)anilino]-3-methoxy-6-methylacridine,
9-[4'-(β-Isopropylaminocarbonyloxyethyl)anilino]-6-methoxy-2-methylacridine,
9-[4'-(β-Isopropylaminocarbonyloxyethyl)anilino]-3,6-dimethoxyacridine,
9-[4'-(β-Isopropylaminocarbonyloxyethyl)anilino]-2,6-dimethylacridine,
9-[4'-(β-Isopropylaminocarbonyloxyethyl)anilino]-2,7-dimethylacridine,
9-[4'-(β-Isopropylaminocarbonyloxyethyl)anilino]-3,6-dimethylacridine,
9-[4'-(β-Isopropylaminocarbonyloxyethyl)anilino]-7-methoxy-2,3-dimethylacridine,
9-[4'-(β-Isopropylaminocarbonyloxyethyl)anilino]-2,6-dimethoxy-7-methylacridine,
9-[4'-(β-Isopropylaminocarbonyloxyethyl)anilino]-2,7-dimethoxy-3-methylacridine,
9-[4'-(β-Isopropylaminocarbonyloxyethyl)anilino]-2,3,7-trimethoxyacridine,
9-[4'-(β-Isopropylaminocarbonyloxyethyl)anilino]-6-methoxy-2,3-dimethylacridine,
9-[4'-(β-Isopropylaminocarbonyloxyethyl)anilino]-3,6-dimethoxy-2-methylacridine,
9-[4'-(β-Isopropylaminocarbonyloxyethyl)anilino]-2,6-dimethoxy-3-methylacridine,
9-[4'-(β-Isopropylaminocarbonyloxyethyl)anilino]-2,3,6-trimethylacridine,
9-[4'-(β-Isopropylaminocarbonyloxyethyl)anilino]-3-methoxy-2,7-dimethylacridine,
9-[4'-(β-Isopropylaminocarbonyloxyethyl)anilino]-2-methoxy-5,7-dimethylacridine,
9-[4'-(β-Isopropylaminocarbonyloxyethyl)anilino]-2,3-dimethoxy-7-methylacridine, 9-[4'-(β-Isopropylaminocarbonyloxyethyl)anilino]-2,3,7-trimethylacridine,
9-[4'-(β-Isopropylaminocarbonyloxyethyl)anilino]-3-methoxy-2,6-dimethylacridine,
9-[4'-(β-Isopropylaminocarbonyloxyethyl)anilino]-2-methoxy-3,6-dimethylacridine,
9-[4'-(β-Isopropylaminocarbonyloxyethyl)anilino]-2,3-dimethoxy-6-methylacridine,
9-[4'-(β-Isopropylaminocarbonyloxyethyl)anilino]-2,3,6-trimethylacridine,
9-[4'-(β-Isopropylaminocarbonyloxyethyl)anilino]-2,3-dimethoxy-6,7-dimethylacridine,
9-[4'-(β-Isopropylaminocarbonyloxyethyl)anilino]-2,3,6-trimethoxy-7-methylacridine,
9-[4'-(β-Isopropylaminocarbonyloxyethyl)anilino]-3-methoxy-2,6,7-trimethylacridine,
9-[4'-(β-Isopropylaminocarbonyloxyethyl)anilino]-2,3,6,7-tetramethylacridine,

Discussion

Basic and planar molecules, such as derivatives of acridine, readily intercalate into DNA. If such molecules can bind to DNA after intercalation, the DNA function should be permanently damaged and result in improved anticancer activity. This invention is made on the basis of the above new concept.

Table 6 lists typical results of in vitro studies on 9-(substituted)anilinoacridines of formula III.

TABLE 6

Inhibitory activity of some of the acridine derivatives of formula III against growth of mouse leukemia L1210 cells.

| Compd. | $R^1$ | $R^2$ | $R^3$ | $R^4$ | $R^5$ | $R^6$ | $R^7$ | $IC_{50}$ (M) |
|---|---|---|---|---|---|---|---|---|
| IIIa | H | H | H | H | $CH_2OH$ | H | H | $4.3 \times 10^{-5}$ |
| IIIb | H | H | H | H | H | $CH_2OH$ | H | $1.4 \times 10^{-8}$ |
| IIIc | H | H | H | H | H | H | $CH_2OH$ | $9.5 \times 10^{-8}$ |
| IIId | H | H | H | H | $(CH_2)_2OH$ | H | H | $6.5 \times 10^{-6}$ |
| IIIe | H | H | H | H | H | $(CH_2)_2OH$ | H | $6.2 \times 10^{-9}$ |
| IIIf | H | H | H | H | H | H | $(CH_2)_2OH$ | $9.9 \times 10^{-9}$ |
| IIIg | H | H | Me | H | H | $CH_2OH$ | H | $8.5 \times 10^{-7}$ |
| IIIh | H | H | H | Me | H | $CH_2OH$ | H | $3.9 \times 10^{-10}$ |
| IIIi | H | H | MeO | H | H | $CH_2OH$ | H | $3.5 \times 10^{-6}$ |
| IIIj | H | H | H | MeO | H | $CH_2OH$ | H | $6.3 \times 10^{-11}$ |
| IIIk | MeO | H | Me | H | H | $CH_2OH$ | H | $5.8 \times 10^{-6}$ |
| IIIl | MeO | H | H | Me | H | $CH_2OH$ | H | $9.2 \times 10^{-7}$ |
| IIIm | MeO | H | MeO | H | H | $CH_2OH$ | H | $3.4 \times 10^{-6}$ |
| IIIn | H | H | MeO | H | H | $(CH_2)_2OH$ | H | $2.3 \times 10^{-11}$ |
| IIIo | H | H | Me | H | H | H | $CH_2OH$ | $1.2 \times 10^{-7}$ |
| IIIp | H | H | H | Me | H | H | $CH_2OH$ | $6.7 \times 10^{-9}$ |
| IIIq | H | H | MeO | H | H | H | $CH_2OH$ | $6.2 \times 10^{-7}$ |
| IIIr | H | H | H | MeO | H | H | $CH_2OH$ | $2.9 \times 10^{-8}$ |
| IIIs | MeO | H | Me | H | H | H | $CH_2OH$ | $5.8 \times 10^{-8}$ |
| IIIt | MeO | H | H | Me | H | H | $CH_2OH$ | $6.5 \times 10^{-7}$ |
| IIIu | MeO | H | MeO | H | H | H | $CH_2OH$ | $3.4 \times 10^{-6}$ |
| IIIv | H | H | H | MeO | H | H | $(CH_2)_2OH$ | $1.8 \times 10^{-8}$ |
| IIIw | MeO | H | MeO | H | H | H | $(CH_2)_2OH$ | $6.9 \times 10^{-7}$ |

9-[4'-(β-Isopropylaminocarbonyloxyethyl)anilino]-2,3,7-trimethoxy-6-methylacridine,
9-[4'-(β-Isopropylaminocarbonyloxyethyl)anilino]-2,3,6,7-tetramethoxyacridine,
9-[4'-(β-Isopropylaminocarbonyloxyethyl)anilino]-2-methoxy-3,6,7-trimethylacridine, Table 7 lists the inhibitor activity of some of the carbamate esters of acridine derivatives having the structure of formula IV against growth of mouse leukemic L1210 cells.

TABLE 7

Antileukemic potency of carbamate esters of acridine derivatives against mouse L1210 cells in vitro.

| Compd. | $R^1$ | $R^2$ | $R^3$ | $R^4$ | position of side chain | n | R | $IC_{50}$ (M) |
|---|---|---|---|---|---|---|---|---|
| IVa | H | H | H | H | 2' | 1 | Me | $8.4 \times 10^{-6}$ |
| IVb | H | H | H | H | 2' | 1 | i-Pr | $9.3 \times 10^{-6}$ |
| IVc | H | H | H | H | 3' | 1 | Me | $4.6 \times 10^{-6}$ |
| IVd | H | H | H | H | 3' | 1 | i-Pr | $9.1 \times 10^{-9}$ |
| IVe | H | H | H | H | 4' | 1 | Me | $3.8 \times 10^{-8}$ |
| IVf | H | H | H | H | 4' | 1 | i-Pr | $1.8 \times 10^{-8}$ |
| IVg | H | H | H | H | 3' | 2 | Me | $5.7 \times 10^{-6}$ |
| IVh | H | H | H | H | 3' | 2 | i-Pr | $9.1 \times 10^{-10}$ |
| IVi | H | H | H | H | 4' | 2 | Me | $3.9 \times 10^{-9}$ |
| IVj | H | H | H | H | 4' | 2 | i-Pr | $4.8 \times 10^{-8}$ |
| IVk | H | MeO | H | H | 3' | 1 | Me | $1.7 \times 10^{-6}$ |
| IVl | H | MeO | H | H | 3' | 1 | i-Pr | $8.9 \times 10^{-7}$ |
| IVm | MeO | H | MeO | H | 3' | 1 | Me | $5.0 \times 10^{-6}$ |
| IVn | MeO | H | MeO | H | 3' | 1 | i-Pr | $4.0 \times 10^{-6}$ |
| IVo | MeO | H | MeO | H | 4' | 1 | Me | $3.6 \times 10^{-6}$ |
| IVp | MeO | H | MeO | H | 4' | 1 | i-Pr | $6.6 \times 10^{-6}$ |
| IVq | MeO | H | MeO | H | 4' | 2 | Me | $2.6 \times 10^{-6}$ |
| IVq | MeO | H | MeO | H | 4' | 2 | i-Pr | $6.3 \times 10^{-6}$ |

It should be noted that carbamate esters IV, in general, exhibit activity less potent than the parent alcohols III in vitro. However, in vivo experiments using female BDF1 mice show that the carbamate esters are far more potent than the corresponding parent alcohols in mice. For example, the benzyl alcohol IIIc gave an excellent IC$_{50}$ value of $9.5 \times 10^{-8}$ (Table 6) but showed only marginal effect on mice inoculated with $1.0 \times 10^6$ L1210 cells with an ILS (increased life span) value of 29% at 100 and 150 mg/kg dose level (see FIG. 2). On the other hand, the corresponding methyl carbamate ester IVc gave good ILS values of 71% and >250% at the dose levels of 100 and 200 mg/kg, respectively.

The process of treating tumors according to this invention comprises administrating to a warm blooded animal having an abnormal proportion of leukocytes or other evidence of a malignancy, a therapeutic nontoxic amount of a compound of the invention such as 9-[4'-(N-methyaminocarbonyloxymethyl)anilino]-acridine, as such or in the form of a pharmaceutically acceptable salt thereof. The invention also provides a pharmaceutical composition in dosages from about 1 to 500 mg/kg of a compound of the invention, per dosage unit, together with a pharmaceutically acceptable nontoxic inert carrier or diluent as described above.

What is claimed is:

1. A compound having the structure:

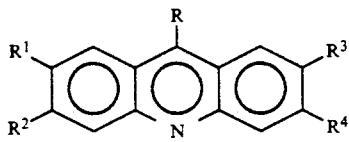

wherein each of $R^1$, $R^2$, $R^3$, and $R^4$ are the same or different and are hydrogen, or a lower alkyl group of from 1–4 carbon atoms, or a lower alkoxy group of from 1–4 carbon atoms, and R is a substituted aniline

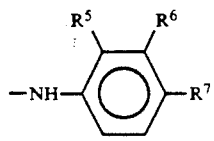

wherein one of $R^5$, $R^6$, or $R^7$ is a carbamate ester having the formula —(CH$_2$)$_n$OCONR'R", n=1–4, wherein R' and R" are the same of different lower alkyl groups of from 1 to 4 carbon atoms, one of R' and R" may be hydrogen, and the remaining groups are hydrogen.

2. A compound of claim 1 selected from the group consisting of:
9-[2'-(Methylaminocarbonyloxymethyl)anilino]acridine,
9-[2'-(Isopropylaminocarbonyloxymethyl)anilino]acridine,
9-[3'-(Methylaminocarbonyloxymethyl)anilino]acridine,
9-[3'-(Methylaminocarbonyloxymethyl)anilino]-2-methoxyacridine,
9-[3'-(Methylaminocarbonyloxymethyl)anilino]-3-methoxyacridine,
9-[3'-(Methylaminocarbonyloxymethyl)anilino]-2-methylacridine,
9-[3'-(Methylaminocarbonyloxymethyl)anilino]-3-methylacridine,
9-[3'-(Methylaminocarbonyloxymethyl)anilino]-2-methoxy-6-methylacridine,
9-[3'-(Methylaminocarbonyloxymethyl)anilino]-2-methoxy-7-methylacridine,
9-[3'-(Methylaminocarbonyloxymethyl)anilino]-2,6-dimethoxyacridine,
9-[3'-(Methylaminocarbonyloxymethyl)anilino]-2,7-dimethoxyacridine,
9-[3'-(Methylaminocarbonyloxymethyl)anilino]-3-methoxy-6-methylacridine,
9-[3'-(Methylaminocarbonyloxymethyl)anilino]-6-methoxy-2-methylacridine,
9-[3'-(Methylaminocarbonyloxymethyl)anilino]-3,6-dimethoxyacridine,
9-[3'-(Methylaminocarbonyloxymethyl)anilino]-2,6-dimethylacridine,
9-[3'-(Methylaminocarbonyloxymethyl)anilino]-3,6-dimethylacridine,
9-[3'-(Methylaminocarbonyloxymethyl)anilino]-7-methoxy-2,3-dimethylacridine,
9-[3'-(Methylaminocarbonyloxymethyl)anilino]-2,6-dimethoxy-7-methylacridine,
9-[3'-{Methylaminocarbonyloxymethyl)anilino]-2,7-dimethoxy-3-methylacridine,
9-[3'-(Methylaminocarbonyloxymethyl)anilino]-2,3,7-trimethoxyacridine,
9-[3'-(Methylaminocarbonyloxymethyl)anilino]-6-methoxy-2,3-dimethylacridine,
9-[3'-(Methylaminocarbonyloxymethyl)anilino]-3,6-dimethoxy-2-methylacridine,
9-[3'-(Methylaminocarbonyloxymethyl)anilino]-2,3,6-trimethoxyacridine,
9-[3'-(Methylaminocarbonyloxymethyl)anilino]-3-methoxy-2,7-dimethylacridine,
9-[3'-(Methylaminocarbonyloxymethyl)anilino]-2-methoxy-3,7-dimethylacridine,
9-[3'-(Methylaminocarbonyloxymethyl)anilino]-2,3-dimethoxy-7-methylacridine,
9-[3'-(Methylaminocarbonyloxymethyl)anilino]-2,3,7-trimethylacridine,
9-[3'-(Methylaminocarbonyloxymethyl)anilino]-3-methoxy-2,6-dimethylacridine,
9-[3'-(Methylaminocarbonyloxymethyl)anilino]-2-methoxy-3,6-dimethylacridine,
9-[3'-(Methylaminocarbonyloxymethyl)anilino]-2,3-dimethoxy-6-methylacridine,
9-[3'-(Methylaminocarbonyloxymethyl)anilino]-2,3,6-trimethylacridine,
9-[3'-(Methylaminocarbonyloxymethyl)anilino]-2,3-dimethoxy-6,7-dimethylacridine,
9-[3'-(Methylaminocarbonyloxymethyl)anilino]-2,3,6-trimethoxy-7-methylacridine,
9-[3'-(Methylaminocarbonyloxymethyl)anilino]-2,3,7-trimethoxy-6-methylacridine,
9-[3'-(Methylaminocarbonyloxymethyl)anilino]-2,3,6,7-tetramethoxyacridine,
9-[3'-(Methylaminocarbonyloxymethyl)anilino]-2-methoxy-3,6,7-trimethylacridine,
9-[3'-(Methylaminocarbonyloxymethyl)anilino]-3-methoxy-2,6,7-trimethylacridine,
9-[3'-(Methylaminocarbonyloxymethyl)anilino]-2,3,6,7-tetramethylacridine,
9-[3'-(Isopropylaminocarbonyloxymethyl)anilino]acridine,
9-[3'-(Isopropylaminocarbonyloxymethyl)anilino]-2-methoxyacridine,
9-[3'-(Isopropylaminocarbonyloxymethyl)anilino]-3-methoxyacridine,
9-[3'-(Isopropylaminocarbonyloxymethyl)anilino]-2-methylacridine, 9-[3'-(Isopropylaminocarbonyloxymethyl)anilino]-3-methylacridine,
9-[3'-(Isopropylaminocarbonyloxymethyl)anilino]-2-methoxy-6-methylacridine,
9-[3'-(Isopropylaminocarbonyloxymethyl)anilino]-2-methoxy-7-methylacridine,
9-[3'-(Isopropylaminocarbonyloxymethyl)anilino]-2,6-dimethoxyacridine,
9-[3'-(Isopropylaminocarbonyloxymethyl)anilino]-3-methoxy-6-methylacridine,
9-[3'-(Isopropylaminocarbonyloxymethyl)anilino]-6-methoxy-2-methylacridine,
9-[3'-(Isopropylaminocarbonyloxymethyl)anilino]-3,6-dimethoxyacridine,
9-[3'-(Isopropylaminocarbonyloxymethyl)anilino]-2,6-dimethylacridine,
9-[3'-(Isopropylaminocarbonyloxymethyl)anilino]-2,7-dimethylacridine,
9-[3'-(Isopropylaminocarbonyloxymethyl)anilino]-3,6-dimethylacridine,
9-[1'-(Isopropylaminocarbonyloxymethyl)anilino]-7-methoxy-2,3-dimethylacridine,
9-[3'-(Isopropylaminocarbonyloxymethyl)anilino]-2,6-dimethoxy-7-dimethylacridine,
9-[3'-(Isopropylaminocarbonyloxymethyl)anilino]-2,7-dimethoxy-3-dimethylacridine,
9-[3'-(Isopropylaminocarbonyloxymethyl)anilino]-2,3,7-trimethoxyacridine,
9-[3'-(Isopropylaminocarbonyloxymethyl)anilino]-6-methoxy-2,3-dimethylacridine,
9-[3'-(Isopropylaminocarbonyloxymethyl)anilino]-3,6-dimethoxy-2-methylacridine,
9-[3'-(Isopropylaminocarbonyloxymethyl)anilino]-2,6-dimethoxy-3-methylacridine,
9-[3'-(Isopropylaminocarbonyloxymethyl)anilino]-2,3,6-trimethoxyacridine,
9-[3'-(Isopropylaminocarbonyloxymethyl)anilino]-3-methoxy-2,7-dimethylacridine,
9-[3'-(Isopropylaminocarbonyloxymethyl)anilino]-2-methoxy-3,7-dimethylacridine,
9-[3'-(Isopropylaminocarbonyloxymethyl)anilino]-2,3-methoxy-7-methylacridine,
9-[3'-(Isopropylaminocarbonyloxymethyl)anilino]-2,3,7-trimethylacridine,
9-[3'-(Isopropylaminocarbonyloxymethyl)anilino]-3-methoxy-2,6-dimethylacridine,
9-[3'-(Isopropylaminocarbonyloxymethyl)anilino]-2-methoxy-3,6-dimethylacridine,
9-[3'-(Isopropylaminocarbonyloxymethyl)anilino]-2,3-dimethoxy-6-methylacridine,
9-[3'-(Isopropylaminocarbonyloxymethyl)anilino]-2,3,6-trimethylacridine,
9-[3'-(Isopropylaminocarbonyloxymethyl)anilino]-2,3-dimethoxy-6,7-dimethylacridine,
9-[3'-(Isopropylaminocarbonyloxymethyl)anilino]-2,3,6-trimethoxy-7-methylacridine,
9-[3'-(Isopropylaminocarbonyloxymethyl)anilino]-2,3,7-trimethoxy-6-methylacridine,
9-[3'-(Isopropylaminocarbonyloxymethyl)anilino]-2,3,6,7-tetramethoxyacridine,
9-[3'-(Isopropylaminocarbonyloxymethyl)anilino]-2-methoxy-3,6,7-trimethylacridine,
9-[3'-(Isopropylaminocarbonyloxymethyl)anilino]-3-methoxy-2,6,7-trimethylacridine,
9-[3'-(Isopropylaminocarbonyloxymethyl)anilino]-2,3,6,7-tetramethylacridine,
9-[4'-(Methylaminocarbonyloxymethyl)anilino]acridine,
9-[4'-(Methylaminocarbonyloxymethyl)anilino]-2-methoxyacridine,
9-[4'-(Methylaminocarbonyloxymethyl)anilino]-3-methoxyacridine,
9-[4'-(Methylaminocarbonyloxymethyl)anilino]-2-methylacridine,
9-[4'-(Methylaminocarbonyloxymethyl)anilino]-3-methylacridine,
9-[4'-(Methylaminocarbonyloxymethyl)anilino]-2-methoxy-6-methylacridine,
9-[4'-(Methylaminocarbonyloxymethyl)anilino]-2-methoxy-7-methylacridine,
9-[4'-(Methylaminocarbonyloxymethyl)anilino]-2,6-dimethoxyacridine,
9-[4'-(Methylaminocarbonyloxymethyl)anilino]-2,7-dimethoxyacridine,
9-[4'-(Methylaminocarbonyloxymethyl)anilino]-3-methoxy-6-methylacridine,
9-[4'-(Methylaminocarbonyloxymethyl)anilino]-6-methoxy-2-methylacridine,
9-[4'-(Methylaminocarbonyloxymethyl)anilino]-3,6-dimethoxyacridine,
9-[4'-(Methylaminocarbonyloxymethyl)anilino]-2,6-dimethylacridine,
9-[4'-(Methylaminocarbonyloxymethyl)anilino]-2,7-dimethylacridine,
9-[4'-(Methylaminocarbonyloxymethyl)anilino]-3,6-dimethylacridine,
9-[4'-(Methylaminocarbonyloxymethyl)anilino]-2,6-dimethoxy-7-methylacridine,
9-[4'-(Methylaminocarbonyloxy-methyl)anilino]-2,7-dimethoxy-7-methylacridine,
9-[4'-(Methylaminocarbonyloxymethyl)anilino]-2,3,7-trimethoxyacridine,
9-[4'-(Methylaminocarbonyloxymethyl)anilino]-6-methoxy-2,3-dimethylacridine,
9-[4'-(Methylaminocarbonyloxymethyl)anilino]-3,6-dimethoxy-2-methylacridine,
9-[4'-(Methylaminocarbonyloxymethyl)anilino]-2,6-dimethoxy-3-methylacridine,
9-[4'-(Methylaminocarbonyloxymethyl)anilino]-2,3,6-trimethoxyacridine,
9-[4'-(Methylaminocarbonyloxymethyl)anilino]-3-methoxy-2,7-dimethylacridine,
9-[4'-(Methylaminocarbonyloxymethyl)anilino]-2-methoxy-3,7-dimethylacridine,
9-[4'-(Methylaminocarbonyloxymethyl)anilino]-2,3-dimethoxy-7-methylacridine,
9-[4'-(Methylaminocarbonyloxymethyl)anilino]-2,3,7-trimethylacridine,
9-[4'-(Methylaminocarbonyloxymethyl)anilino]-3-methoxy-2,6-dimethylacridine,
9-[4'-(Methylaminocarbonyloxymethyl)anilino]-2-methoxy-3,6-dimethylacridine,
9-[4'-(Methylaminocarbonyloxymethyl)anilino]-2,3-dimethoxy-6-methylacridine,
9-[4'-(Methylaminocarbonyloxymethyl)anilino]-2,3,6-trimethylacridine,
9-[4'-(Methylaminocarbonyloxymethyl)anilino]-2,3-dimethoxy-6,7-dimethylacridine,
9-[4'-(Methylaminocarbonyloxymethyl)anilino]-2,3,6-trimethoxy-7-methylacridine,
9-[4'-(Methylaminocarbonyloxymethyl)anilino]-2,3,7-trimethoxy-6-methylacridine,
9-[4'-(Methylaminocarbonyloxymethyl)anilino]-2,3,6,7-tetramethoxyacridine,
9-[4'-(Methylaminocarbonyloxymethyl)anilino]-2-methoxy-3,6,7-trimethylacridine, 9-[4'-(Methylaminocarbonyloxymethyl)anilino]-3-methoxy-2,6,7-trimethylacridine,
9-[4'-(Methylaminocarbonyloxymethyl)anilino]-2,3,6,7-tetramethylacridine,
9-[4'-(Isopropylaminocarbonyloxymethyl)anilino]acridine,
9-[4'-(Isopropylaminocarbonyloxymethyl)anilino]-2-methoxyacridine,
9-[4'-(Isopropylaminocarbonyloxymethyl)anilino]-3-methoxyacridine,
9-[4'-(Isopropylaminocarbonyloxymethyl)anilino]-2-methylacridine,
9-[4'-(Isopropylaminocarbonyloxymethyl)anilino]-3-methylacridine,
9-[4'-(Isopropylaminocarbonyloxymethyl)anilino]-2-methoxy-6-methylacridine,
9-[4'-(Isopropylaminocarbonyloxymethyl)anilino]-2-methoxy-7-methylacridine,
9-[4'-(Isopropylaminocarbonyloxymethyl)anilino]-2,6-dimethoxyacridine,
9-[4'-(Isopropylaminocarbonyloxymethyl)anilino]-2,7-dimethoxyacridine,
9-[4'-(Isopropylaminocarbonyloxymethyl)anilino]-3-methoxy-6-methylacridine,
9-[4'-(Isopropylaminocarbonyloxymethyl)anilino]-6-methoxy-2-methylacridine,
9-[4'-(Isopropylaminocarbonyloxymethyl)anilino]-3,6-dimethoxyacridine,
9-[4'-(Isopropylaminocarbonyloxymethyl)anilino]-2,6-dimethylacridine,
9-[4'-(Isopropylaminocarbonyloxymethyl)anilino]-2,7-dimethylacridine,
9-[4'-(Isopropylaminocarbonyloxymethyl)anilino]-3,6-dimethylacridine,
9-[4'-(Isopropylaminocarbonyloxymethyl)anilino]-7-methoxy-2,3-dimethylacridine,
9-[4'-(Isopropylaminocarbonyloxymethyl)anilino]-2,6-dimethoxy-7-dimethylacridine,
9-[4'-(Isopropylaminocarbonyloxymethyl)anilino]-2,7-dimethoxy-3-methylacridine,
9-[4'-(Isopropylaminocarbonyloxymethyl)anilino]-2,3,7-trimethoxyacridine,
9-[4'-(Isopropylaminocarbonyloxymethyl)anilino]-6-methoxy-2,3-dimethylacridine,
9-[4'-(Isopropylaminocarbonyloxymethyl)anilino]-3,6-dimethoxy-2-methylacridine,
9-[4'-(Isopropylaminocarbonyloxymethyl)anilino]-2,6-dimethoxy-3-methylacridine,
9-[4'-(Isopropylaminocarbonyloxymethyl)anilino]-2,3,6-trimethoxyacridine,
9-[4'-(Isopropylaminocarbonyloxymethyl)anilino]-3-methoxy-2,7-dimethylacridine,
9-[4'-(Isopropylaminocarbonyloxymethyl)anilino]-2-[methoxy-3,7-dimethylacridine,
9-[4'-(Isopropylaminocarbonyloxymethyl)anilino]-2,3-methoxy-7-methylacridine,
9-[4'-(Isopropylaminocarbonyloxymethyl)anilino]-2,3,7-trimethylacridine,
9-[4'-(Isopropylaminocarbonyloxymethyl)anilino]-3-methoxy-2,6-dimethylacridine,
9-[4'-(Isopropylaminocarbonyloxymethyl)anilino]-2-methoxy-3,6-dimethylacridine,
9-[4'-(Isopropylaminocarbonyloxymethyl)anilino]-2,3-dimethoxy-6-methylacridine,
9-[4'-(Isopropylaminocarbonyloxymethyl)anilino]-2,3,6-trimethylacridine,
9-[4'-(Isopropylaminocarbonyloxymethyl)anilino]-2,3-dimethoxy-6,7-dimethylacridine,
9-[4'-(Isopropylaminocarbonyloxymethyl)anilino]-2,3,6-trimethoxy-7-methylacridine,
9-[4'-(Isopropylaminocarbonyloxymethyl)anilino]-2,3,7-trimethoxy-6-methylacridine,
9-[4'-(Isopropylaminocarbonyloxymethyl)anilino]-2,3,6,7-tetramethoxyacridine,
9-[4'-(Isopropylaminocarbonyloxymethyl)anilino]-2-methoxy-3,6,7-trimethylacridine,
9-[4'-(Isopropylaminocarbonyloxymethyl)anilino]-3-methoxy-2,6,7-trimethylacridine,
9-[4'-(Isopropylaminocarbonyloxymethyl)anilino]-2,3,6,7-tetramethylacridine,
9-[2'-(β-Methylaminocarbonyloxyethyl)anilino]acridine,
9-[2'-(β-Isopropylaminocarbonyloxyethyl)anilino]acridine,
9-[3'-(β-Methylaminocarbonyloxyethyl)anilino]acridine,
9-[3'-(β-Methylaminocarbonyloxyethyl)anilino]-2-methoxyacridine,
9-[3'-(β-Methylaminocarbonyloxyethyl)anilino]-3-methoxyacridine,
9-[3'-(β-Methylaminocarbonyloxyethyl)anilino]-2-methylacridine,
9-[3'-(β-Methylaminocarbonyloxyethyl)anilino]-3-methylacridine,
9-[3'-(β-Methylaminocarbonyloxyethyl)anilino]-2-methoxy-6-methylacridine,
9-[3'-(β-Methylaminocarbonyloxyethyl)anilino]-2-methoxy-7-methylacridine,
9-[3'-(β-Methylaminocarbonyloxyethyl)anilino]-2,6-dimethoxyacridine,
9-[3'-(β-Methylaminocarbonyloxyethyl)anilino]-2,7-dimethoxyacridine,
9-[3'-(β-Methylaminocarbonyloxyethyl)anilino]-3-methoxy-6-methylacridine,
9-[3'-(β-Methylaminocarbonyloxyethyl)anilino]-6-methoxy-2-methylacridine,
9-[3'-(β-Methylaminocarbonyloxyethyl)anilino]-3,6-dimethoxyacridine,
9-[3'-(β-Methylaminocarbonyloxyethyl)anilino]-2,6-dimethylacridine,
9-[3'-(β-Methylaminocarbonyloxyethyl)anilino]-3,6-dimethylacridine,
9-[3'-(β-Methylaminocarbonyloxyethyl)anilino]-7-methoxy-2,3-dimethylacridine,
9-[3'-(β-Methylaminocarbonyloxyethyl)anilino]-2,6-dimethoxy-7-methylacridine,
9-[3'-(β-Methylaminocarbonyloxyethyl)anilino]-2,7-dimethoxy-3-methylacridine,
9-[3'-(β-Methylaminocarbonyloxyethyl)anilino]-2,3,7-trimethoxyacridine,
9-[3'-(β-Methylaminocarbonyloxyethyl)anilino]-6-methoxy-2,3-dimethylacridine,
9-[3'-(β-Methylaminocarbonyloxyethyl)anilino]-3,6-dimethoxy-2-methylacridine,
9-[3'-(β-Methylaminocarbonyloxyethyl)anilino]-2,3,6-trimethoxyacridine,
9-[3'-(β-Methylaminocarbonyloxyethyl)anilino]-3-methoxy-2,7-dimethylacridine,
9-[3'-(β-Methylaminocarbonyloxyethyl)anilino]-2-methoxy-3,7-dimethylacridine,
9-[3'-(β-Methylaminocarbonyloxyethyl)anilino]-2,3-dimethoxy-7-methylacridine,
9-[3'-(β-Methylaminocarbonyloxyethyl)anilino]-2,3,7-trimethylacridine,
9-[3'-(β-Methylaminocarbonyloxyethyl)anilino]-3-methoxy-2,6-dimethylacridine, 9-[3'-(β-Methylaminocarbonyloxyethyl)anilino]-2-methoxy-3,6-dimethylacridine,
9-[3'-(β-Methylaminocarbonyloxyethyl)anilino]-2,3-dimethoxy-6-methylacridine,
9-[3'-(β-Methylaminocarbonyloxyethyl)anilino]-2,3,6-trimethylacridine,
9-[3'-(β-Methylaminocarbonyloxyethyl)anilino]-2,3-dimethoxy-6,7-dimethylacridine,
9-[3'-(β-Methylaminocarbonyloxyethyl)anilino]-2,3,6-trimethoxy-7-methylacridine,
9-[3'-(β-Methylaminocarbonyloxyethyl)anilino]-2,3,7-trimethoxy-6-methylacridine,
9-[3'-(β-Methylaminocarbonyloxyethyl)anilino]-2,3,6,7-tetramethoxyacridine,
9-[3'-(β-Methylaminocarbonyloxyethyl)anilino]-2-methoxy-3,6,7-trimethylacridine,
9-[3'-(β-Methylaminocarbonyloxyethyl)anilino]-3-methoxy-2,6,7-trimethylacridine,
9-[3'-(β-Methylaminocarbonyloxyethyl)anilino]-2,3,6,7-tetramethylacridine,
9-[3'-(β-Isopropylaminocarbonyloxyethyl)anilino]acridine,
9-[3'-(β-Isopropylamino#pqbonyloxyethyl)anilino]-2-methoxyacridine,
9-[3'-(β-Isopropylaminocarbonyloxyethyl)anilino]-3-methoxyacridine,
9-[3'-(β-Isopropylaminocarbonyloxyethyl)anilino]-2-methylacridine,
9-[3'-(β-Isopropylaminocarbonyloxyethyl)anilino]-3-methylacridine,
9-[3'-(β-Isopropylaminocarbonyloxyethyl)anilino]-2-methoxy-6-methylacridine,
9-[3'-(β-Isopropylaminocarbonyloxyethyl)anilino]-2-methoxy-7-methylacridine,
9-[3'-(β-Isopropylaminocarbonyloxyethyl)anilino]-2,6-dimethoxyacridine,
9-[3'-(β-Isopropylaminocarbonyloxyethyl)anilino]-2,7-dimethoxyacridine,
9-[3'-(β-Isopropylaminocarbonyloxyethyl)anilino]-3-methoxy-6-methylacridine,
9-[3'-(β-Isopropylaminocarbonyloxyethyl)anilino]-6-methoxy-2-methylacridine,
9-[3'-(β-Isopropylaminocarbonyloxyethyl)anilino]-3,6-dimethoxyacridine,
9-[3'-(β-Isopropylaminocarbonyloxyethyl)anilino]-2,6-dimethylacridine,
9-[3'-(β-Isopropylaminocarbonyloxyethyl)anilino]-2,7-dimethylacridine,
9-[3'-(β-Isopropylaminocarbonyloxyethyl)anilino]-3,6-dimethylacridine,
9-[3'-(β-Isopropylaminocarbonyloxyethyl)anilino]-7-methoxy-2,3-dimethylacridine,
9-[3'-(β-Isopropylaminocarbonyloxyethyl)anilino]-2,6-dimethoxy-7-dimethylacridine,
9-[3'-(β-Isopropylaminocarbonyloxyethyl)anilino]-2,7-dimethoxy-3-methylacridine,
9-[3'-(β-Isopropylaminocarbonyloxyethyl)anilino]-2,3,6-trimethoxyacridine,
9-[3'-(β-Isopropylaminocarbonyloxyethyl)anilino]-6-methoxy-2,3-dimethylacridine,
9-[3'-(β-Isopropylaminocarbonyloxyethyl)anilino]-3,6-dimethoxy-2-methylacridine,
9-[3'-(β-Isopropylaminocarbonyloxyethyl)anilino]-2,6-dimethoxy-3-methylacridine,
9-[3'-(β-Isopropylaminocarbonyloxyethyl)anilino]-2,3,7-trimethoxyacridine,
9-[3'-(β-Isopropylaminocarbonyloxyethyl)anilino]-3-methoxy-2,7-dimethylacridine,
9-[3'-(β-Isopropylaminocarbonyloxyethyl)anilino]-2-methoxy-3,7-dimethylacridine,
9-[3'-(β-Isopropylaminocarbonyloxyethyl)anilino]-2,3-dimethoxy-7-methylacridine,
9-[3'-(β-Isopropylaminocarbonyloxyethyl)anilino]-2,3,7-trimethylacridine,
9-[3'-(β-Isopropylaminocarbonyloxyethyl)anilino]-3-methoxy-2,6-dimethylacridine,
9-[3'-(β-Isopropylaminocarbonyloxyethyl)anilino]-2-methoxy-3,6-dimethylacridine,
9-[3'-(β-Isopropylaminocarbonyloxyethyl)anilino]-2,3-dimethoxy-6-methylacridine,
9-[3'-(β-Isopropylaminocarbonyloxyethyl)anilino]-2,3,6-trimethylacridine,
9-[3'-(β-Isopropylaminocarbonyloxyethyl)anilino]-2,3-dimethoxy-6,7-dimethylacridine,
9-[3'-(β-Isopropylaminocarbonyloxyethyl)anilino]-2,3,6-trimethoxy-7-methylacridine,
9-[3'-(β-Isopropylaminocarbonyloxyethyl)anilino]-2,3,7-trimethoxy-6-methylacridine,
9-[3'-(β-Isopropylaminocarbonyloxyethyl)anilino]-2,3,6,7-tetramethoxyacridine,
9-[3'-(β-Isopropylaminocarbonyloxyethyl)anilino]-2-methoxy-3,6,7-trimethylacridine,
9-[3'-(β-Isopropylaminocarbonyloxyethyl)anilino]-3-methoxy-2,6,7-trimethylacridine,
9-[3'-(β-Isopropylaminocarbonyloxyethyl)anilino]-2,3,6,7-tetramethylacridine,
9-[4'-(β-Methylaminocarbonyloxyethyl)anilino]acridine,
9-[4'-(β-Methylaminocarbonyloxyethyl)anilino]-2-methoxyacridine,
9-[4'-(β-Methylaminocarbonyloxyethyl)anilino]-3-methoxyacridine,
9-[4'-(β-Methylaminocarbonyloxyethyl)anilino]-2-methylacridine,
9-[4'-(β-Methylaminocarbonyloxyethyl)anilino]-3-methylacridine,
9-[4'-(β-Methylaminocarbonyloxyethyl)anilino]-2-methoxy-6-methylacridine,
9-[4'-(β-Methylaminocarbonyloxyethyl)anilino]-2-methoxy-7-methylacridine,
9-[4'-(β-Methylaminocarbonyloxyethyl)anilino]-2,6-dimethoxyacridine,
9-[4'-(β-Methylaminocarbonyloxyethyl)anilino]-2,7-dimethoxyacridine,
9-[4'-(β-Methylaminocarbonyloxyethyl)anilino]-3-methoxy-6-methylacridine,
9-[4'-(β-Methylaminocarbonyloxyethyl)anilino]-6-methoxy-2-methylacridine,
9-[4'-(β-Methylaminocarbonyloxyethyl)anilino]-3,6-dimethoxyacridine,
9-[4'-(β-Methylaminocarbonyloxyethyl)anilino]-2,6-dimethylacridine,
9-[4'-(β-Methylaminocarbonyloxyethyl)anilino]-2,7-dimethylacridine,
9-[4'-(β-Methylaminocarbonyloxyethyl)anilino]-3,6-dimethylacridine,
9-[4'-(β-Methylaminocarbonyloxyethyl)anilino]-2,6-dimethoxy-7-methylacridine,
9-[4'-(β-Methylaminocarbonyloxyethyl)anilino]-2,7-dimethoxy-3-methylacridine,
9-[4'-(β-Methylaminocarbonyloxyethyl)anilino]-2,3,7-trimethoxyacridine,
9-[4'-(β-Methylaminocarbonyloxyethyl)anilino]-6-methoxy-2,3-dimethylacridine,
9-[4'-(β-Methylaminocarbonyloxyethyl)anilino]-3,6-dimethoxy-2-methylacridine, 9-[4'-(β-Methylaminocarbonyloxyethyl)anilino]-2,6-dimethoxy-3-methylacridine,
9-[4'-(β-Methylaminocarbonyloxyethyl)anilino]-2,3,6-trimethoxyacridine,
9-[4'-(β-Methylaminocarbonyloxyethyl)anilino]-3-methoxy-2,7-dimethylacridine,
9-[4'-(β-Methylaminocarbonyloxyethyl)anilino]-2-methoxy-3,7-dimethylacridine,
9-[4'-(β-Methylaminocarbonyloxyethyl)anilino]-2,3-dimethoxy-7-methylacridine,
9-[4'-(β-Methylaminocarbonyloxyethyl)anilino]-2,3,7-trimethylacridine,
9-[4'-(β-Methylaminocarbonyloxyethyl)anilino]-3-methoxy-2,6-dimethylacridine,
9-[4'-(β-Methylaminocarbonyloxyethyl)anilino]-2-methoxy-3,6-dimethylacridine,
9-[4'-(β-Methylaminocarbonyloxyethyl)anilino]-2,3-dimethoxy-6-methylacridine,
9-[4'-(β-Methylaminocarbonyloxyethyl)anilino]-2,3,6-trimethylacridine,
9-[4'-(β-Methylaminocarbonyloxyethyl)anilino]-2,3-dimethoxy-6,7-dimethylacridine,
9-[4'-(β-Methylaminocarbonyloxyethyl)anilino]-2,3,6-trimethoxy-7-methylacridine,
9-[4'-(β-Methylaminocarbonyloxyethyl)anilino]-2,3,7-trimethoxy-6-methylacridine,
9-[4'-(β-Methylaminocarbonyloxyethyl)anilino]-2,3,6,7-tetramethoxyacridine,
9-[4'-(β-Methylaminocarbonyloxyethyl)anilino]-2-methoxy-3,6,7-trimethylacridine,
9-[4'-(β-Methylaminocarbonyloxyethyl)anilino]-3-methoxy-2,6,7-trimethylacridine,
9-[4'-(β-Methylaminocarbonyloxyethyl)anilino]-2,3,6,7-tetramethylacridine,
9-[4'-(β-Isopropylaminocarbonyloxyethyl)anilino]acridine,
9-[4'-(β-Isopropylaminocarbonyloxyethyl)anilino]-2-methoxyacridine,
9-[4'-(β-Isopropylaminocarbonyloxyethyl)anilino]-3-methoxyacridine,
9-[4'-(β-Isopropylaminocarbonyloxyethyl)anilino]-2-methylacridine,
9-[4'-(β-Isopropylaminocarbonyloxyethyl)anilino]-3-methylacridine,
9-[4'-(β-Isopropylaminocarbonyloxyethyl)anilino]-2-methoxy-6-methylacridine,
9-[4'-(β-Isopropylaminocarbonyloxyethyl)anilino]-2-methoxy-7-methylacridine,
9-[4'-(β-Isopropylaminocarbonyloxyethyl)anilino]-2,6-dimethoxyacridine,
9-[4'-(β-Isopropylaminocarbonyloxyethyl)anilino]-2,7-dimethoxyacridine,
9-[4'-(β-Isopropylaminocarbonyloxyethyl)anilino]-3-methoxy-6-methylacridine,
9-[4'-(β-Isopropylaminocarbonyloxyethyl)anilino]-6-methoxy-2-methylacridine,
9-[4'-(β-Isopropylaminocarbonyloxyethyl)anilino]-3,6-dimethoxyacridine,
9-[4'-(β-Isopropylaminocarbonyloxyethyl)anilino]-2,6-dimethylacridine,
9-[4'-(β-Isopropylaminocarbonyloxyethyl)anilino]-2,7-dimethylacridine,
9-[4'-(β-Isopropylaminocarbonyloxyethyl)anilino]-3,6-dimethylacridine,
9-[4'-(β-Isopropylaminocarbonyloxyethyl)anilino]-7-methoxy-2,3-dimethylacridine,
9-[4'-(β-Isopropylaminocarbonyloxyethyl)anilino]-2,6-dimethoxy-7-methylacridine,
9-[4'-(β-Isopropylaminocarbonyloxyethyl)anilino]-2,7-dimethoxy-3-methylacridine,
9-[4'-(β-Isopropylaminocarbonyloxyethyl)anilino]-2,3,7-trimethoxyacridine,
9-[4'-(β-Isopropylaminocarbonyloxyethyl)anilino]-6-methoxy-2,3-dimethylacridine,
9-[4'-(β-Isopropylaminocarbonyloxyethyl)anilino]-3,6-dimethoxy-2-methylacridine,
9-[4'-(β-Isopropylaminocarbonyloxyethyl)anilino]-2,6-dimethoxy-3-methylacridine,
9-[4'-(β-Isopropylaminocarbonyloxyethyl)anilino]-2,3,6-trimethoxyacridine,
9-[4'-(β-Isopropylaminocarbonyloxyethyl)anilino]-3-methoxy-2,7-dimethylacridine,
9-[4'-(β-Isopropylaminocarbonyloxyethyl)anilino]-2-methoxy-5,7-dimethylacridine,
9-[4'-(β-Isopropylaminocarbonyloxyethyl)anilino]-2,3-dimethoxy-7-methylacridine,
9-[4'-(β-Isopropylaminocarbonyloxyethyl)anilino]-2,3,7-trimethylacridine,
9-[4'-(β-Isopropylaminocarbonyloxyethyl)anilino]-3-methoxy-2,6-dimethylacridine,
9-[4'-(β-Isopropylaminocarbonyloxyethyl)anilino]-2-methoxy-3,6-dimethylacridine,
9-[4'-(β-Isopropylaminocarbonyloxyethyl)anilino]-2,3-dimethoxy-6-methylacridine,
9-[4'-(β-Isopropylaminocarbonyloxyethyl)anilino]-2,3,6-trimethylacridine,
9-[4'-(β-Isopropylaminocarbonyloxyethyl)anilino]-2,3-dimethoxy-6,7-dimethylacridine,
9-[4'-(β-Isopropylaminocarbonyloxyethyl)anilino]-2,3,6-trimethoxy-7-methylacridine,
9-[4'-(β-Isopropylaminocarbonyloxyethyl)anilino]-2,3,7-trimethoxy-6-methylacridine,
9-[4'-(β-Isopropylaminocarbonyloxyethyl)anilino]-2,3,6,7-tetramethoxyacridine,
9-[4'-(β-Isopropylaminocarbonyloxyethyl)anilino]-2-methoxy-3,6,7-trimethylacridine,
9-[4'-(β-Isopropylaminocarbonyloxyethyl)anilino]-3-methoxy-2,6,7-trimethylacridine,
9-[4'-(β-Isopropylaminocarbonyloxyethyl)anilino]-2,3,6,7-tetramethylacridine.

3. A pharmaceutical composition comprising an amount of the compound of claim 1, or a salt thereof, effective to inhibit the growth of tumor cells and a physiologically acceptable carrier.

4. A method of treating a subject having a tumor which comprises administering to the subject an amount of a composition of claim 3, effective to inhibit the growth of tumor cells.

5. A method of inhibiting the growth of tumor cells which comprises contacting the cells with an amount of a compound of claim 1 effective to inhibit the growth of tumor cells.

* * * * *